US006713081B2

(12) United States Patent
Robinson et al.

(10) Patent No.: US 6,713,081 B2
(45) Date of Patent: Mar. 30, 2004

(54) OCULAR THERAPEUTIC AGENT DELIVERY DEVICES AND METHODS FOR MAKING AND USING SUCH DEVICES

(75) Inventors: Michael R. Robinson, Kensington, MD (US); Karl G. Csaky, Kensington, MD (US); Peng Yuan, Rockville, MD (US); Cynthia Sung, Silver Spring, MD (US); Robert B. Nussenblatt, Bethesda, MD (US); Janine A. Smith, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/808,149

(22) Filed: Mar. 15, 2001

(65) Prior Publication Data

US 2003/0175324 A1 Sep. 18, 2003

(51) Int. Cl.[7] .................................................. A61F 2/00
(52) U.S. Cl. ..................... 424/427; 424/422; 424/423; 424/424; 424/425; 424/426; 424/428; 424/484; 424/485; 424/486; 424/487; 424/488; 424/78.04
(58) Field of Search ................ 424/422–427, 424/484, 485, 486, 487, 488, 78.04

(56) References Cited

U.S. PATENT DOCUMENTS

| | | |
|---|---|---|
| 3,960,150 A * | 6/1976 | Hussain et al. ............. 128/260 |
| 4,014,335 A | 3/1977 | Arnold ....................... 128/260 |
| 4,815,690 A | 3/1989 | Shepherd ...................... 249/82 |
| 4,921,908 A | 5/1990 | Ofstead ........................ 525/61 |
| 5,098,443 A | 3/1992 | Parel et al. ..................... 623/4 |
| 5,294,604 A | 3/1994 | Nussenblatt et al. .......... 514/11 |
| 5,322,691 A | 6/1994 | Darougar et al. ............ 424/427 |
| 5,378,475 A | 1/1995 | Smith et al. ................. 424/473 |
| 5,443,505 A | 8/1995 | Wong et al. .................... 623/4 |
| 5,504,074 A | 4/1996 | D'Amato et al. ........... 514/182 |
| 5,521,168 A | 5/1996 | Clark |
| 5,725,493 A | 3/1998 | Avery et al. .................... 604/9 |
| 5,773,019 A | 6/1998 | Ashton et al. .............. 424/423 |
| 5,773,021 A | 6/1998 | Gurtler et al. .............. 424/427 |
| 5,928,662 A | 7/1999 | Phillips ...................... 424/427 |

OTHER PUBLICATIONS

Robinson, M., et al., Sustained–released Biodegradable Subconjunctival Implants for Long Term Delivery of Cyclosporin A, Abstract presented at ARVO Annual Meeting, Ft. Lauderdale, Florida, U.S.A., May 9–14, 1999.

(List continued on next page.)

Primary Examiner—Thurman K. Page
Assistant Examiner—Lakshmi Channavajjala
(74) Attorney, Agent, or Firm—Leydig, Voit & Mayer, Ltd.

(57) ABSTRACT

Ocular implant devices for the delivery of a therapeutic agent to an eye in a controlled and sustained manner. Dual mode and single mode drug delivery devices are illustrated and described. Implants suitable for subconjunctival placement are described. Implants suitable for intravitreal placement also are described. The invention also includes fabrication and implementation techniques associated with the unique ocular implant devices that are presented herein.

18 Claims, 27 Drawing Sheets

OTHER PUBLICATIONS

Ross, M., et al., Sustained–release Intraocular Implant for 2–Methoxyestradiol; an Angiostatic Agent for the Treatment of Choroidal Neovascularization, Abstract presented at ARVO Annual Meeting, Ft. Lauderdale, Florida, U.S.A., Apr. 30–May 5, 2000.

Robinson, M., et al., "Sustained–released Intraocular Implant for Carboxyamide–Amino–Imidizole; a Novel Angiostatic Agent", Abstract presented at ARVO Annual Meeting, Ft. Lauderdale, Florida, U.S.A., Apr. 30–May 5, 2000.

Whitcup, S., et al., Sustained–released Methotrexate Implants for the Treatment of Intraocular Lymphoma, Abstract presented at ARVO Annual Meeting, Ft. Lauderdale, Florida, U.S.A., Apr. 30–May 5, 2000.

King, B., et al., Intraocular Micro–Implants Releasing Triamcinolone Acetonide for Use in Rat Models, Abstract presented at ARVO Annual Meeting, Ft. Lauderdale, Florida, U.S.A., Apr. 30–May 5, 2000.

Velez, G., et al., Thalidomide Analogue (EM–138) Sustained–release Implants to Treat Choroidal Neovascularization Associated with Macular Degeneration, Abstract presented at ARVO Annual Meeting, Ft. Lauderdale, Florida, U.S.A., Apr. 30–May 5, 2000.

Jones, L., et al., Acetazolamide Release Rates from Intraocular Lenses, Abstract presented at ARVO Annual Meeting, Ft. Lauderdale, Florida, U.S.A., Apr. 30–May 5, 2000.

* cited by examiner single mode dual mode

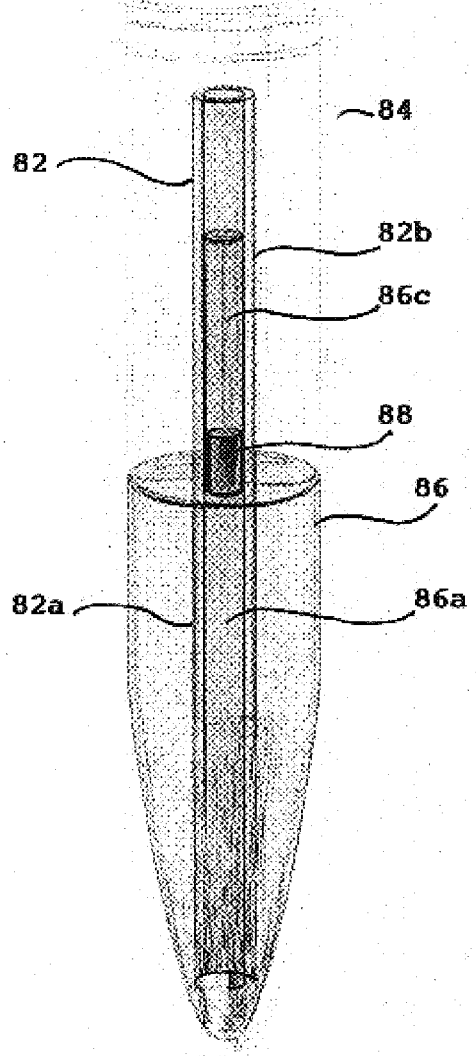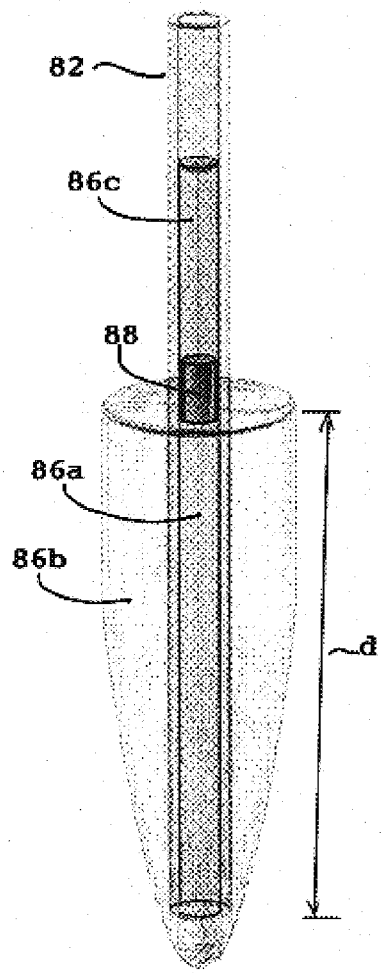

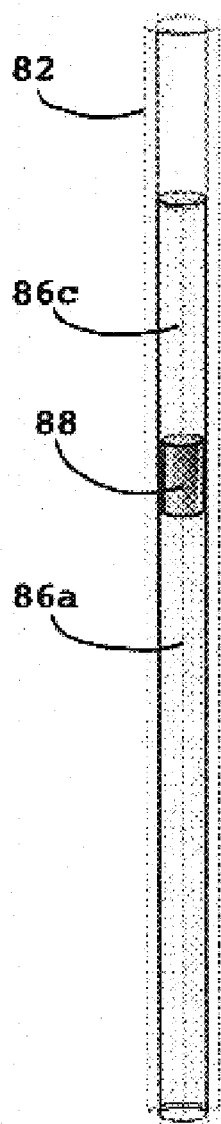
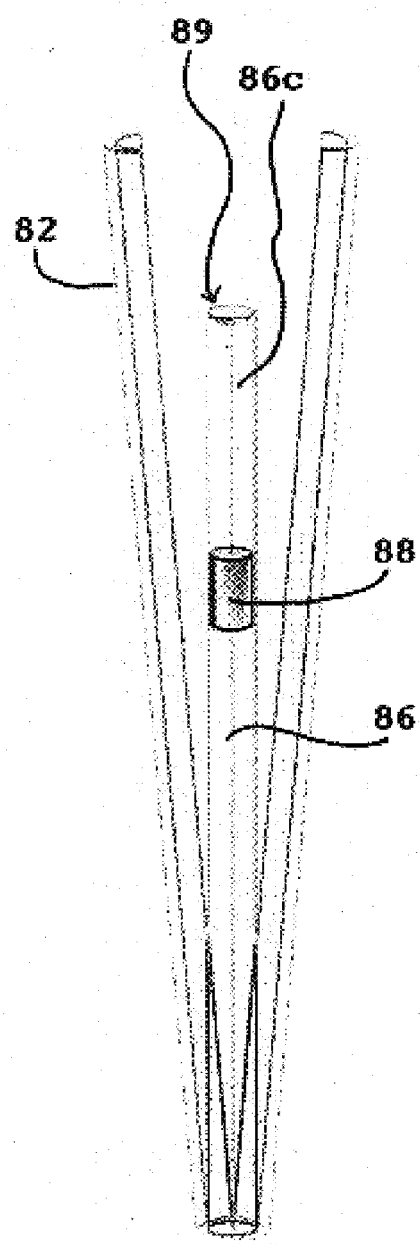
FIG. 8F
FIG. 8G 89
86c
88
86

89

Top view

3-D view

Front view

Cure Delay (time)

0 min.

30 min.

| Thickness of coating around pellet | Mean Release Rates (ug/day) | Predicted Steady State Concentration (uM) | Implant Life Span (yrs) | Durability |
|---|---|---|---|---|
| 0.20 mm | 11.25 | 1.55 | 2.44 | poor |
| 0.36 mm | 6.47 | 0.89 | 4.24 | good |
| 0.70 mm | 5.02 | 0.69 | 5.46 | good |

OCULAR THERAPEUTIC AGENT DELIVERY DEVICES AND METHODS FOR MAKING AND USING SUCH DEVICES

FIELD OF THE INVENTION

The present invention generally relates to local therapies for the eye and, more particularly, to controlled-release ocular implant devices, including methods for making and using such devices, for delivery of therapeutic agents to the eye.

BACKGROUND OF THE INVENTION

In the treatment of many diseases and disorders of the eye, and especially in the case of degenerative or persistent conditions, implantable sustained-release delivery devices have been desired that would continuously administer a therapeutic agent to the eye for a prolonged period of time.

Local ocular implants of a wide variety of constructions and placements have been proposed heretofore for dispensing a therapeutic drug to the eye.

For instance, U.S. Pat. No. 4,014,335 describes an ocular drug delivery device placed in the cul-de-sac between the sclera and lower eyelid for administering the drug and acting as a reservoir. The ocular device is characterized therein as administering drug to the eye in a controlled, continuous dosage rate over a prolonged time. To accomplish this, the ocular device comprises a three-layered laminate of polymeric materials holding the drug in a central reservoir region of the laminate. The drug diffuses from the reservoir through at least one of the polymeric layers of the laminate.

U.S. Pat. No. 5,773,021 describes bioadhesive ophthalmic inserts that are placed in the conjunctival sac, in which the inserts are prepared by extrusion, thermoforming, or heat compression of a polymeric material matrix and the drug to be delivered. The polymeric matrix comprises a water-soluble biocompatible polymer, such as hydroxyalkyl celluloses, maltodextrins, chitosans, modified starches or polyvinyl alcohols; a water-insoluble biocompatible polymer such as an alkyl cellulose; and where applicable a bioadhesive polymer such as polyvinyl carboxylic acid type polymers or certain bioadhesive polysaccharides or derivatives thereof. The ophthalmic inserts are characterized therein as intended for the prolonged and controlled release of a medicinal substance.

U.S. Pat. No. 5,773,019 describes a continuous release drug delivery implant which, among other mentioned places, can be mounted either on the outer surface of the eye or within the eye. A drug core is covered by a polymer coating layer that is permeable to the low solubility agent without being release rate limiting. Descriptions include a coating of cyclosporine A (CsA) drug cores with one or multiple coatings of polyvinyl alcohol solution, followed by heating to 110, 104 or 120° C., presumably to cross link and harden the coating(s) in place around the core. Also described is a implant prepared by fixing a pellet directly over a smaller hole formed in a silicone film, followed by a suture being placed around the pellet in a gapped relationship thereto, and then the entire assembly is coated again with silicone to form the implant. The ocular device is characterized therein as giving a continuous release to an affected area, once implanted, and producing long-term sustained tissue and vitreous levels at relatively low concentrations.

U.S. Pat. No. 5,378,475 describes a sustained-release implant for insertion into the vitreous of the eye. The implant has a first impermeable coating, such as ethylene vinyl acetate, surrounding most, but not all, of a drug reservoir and a second permeable coating, such as a permeable crosslinked polyvinyl alcohol, disposed over the first coating including the region where the first coating does not cover the drug reservoir, to provide a location through which the drug can diffuse out of the implant. The implant also has a tab which can be used to suture the device in place in the eye. The implant devices are prepared by applying coating solutions, such as by dipping, spraying or brushing, of the various coating layers around the drug reservoir.

U.S. Pat. No. 5,725,493 describes an ocular implant device for providing drugs to the vitreous cavity over a period of time. The drug reservoir is attached to the outside of the eye with a passageway permitting medicament to enter the vitreous cavity of the eye. The above-listing of publications describing prior ocular implant systems is intended to be only illustrative in nature, and not exhaustive.

Local ocular implants avoid the shortcomings and complications that can arise from systemic therapies of eye disorders. For instance, oral therapies for the eye fail to provide sustained-release of the drug into the eye. Instead, oral therapies often only result in negligible actual absorption of the drug in the ocular tissues due to low bioavailability of the drug. Ocular drug levels following systemic administration of drugs is usually limited by the blood/ocular barriers (i.e., tight junctions between the endothelial cells of the capillaries) limit drugs entering the eye via systemic circulation. In addition, variable gastrointestinal drug absorption and/or liver metabolism of the medications can lead to dose to dose and inter-individual variations in vitreous drug levels. Moreover, adverse side effects have been associated with systemic administration of certain drugs to the eyes.

For instance, systemic treatments of the eye using the immune response modifier cyclosporine A (CsA) have the potential to cause nephrotoxicity or increase the risk of opportunistic infections, among other concerns. This is unfortunate since CsA is a recognized effective active agent for treatment of a wide variety of eye diseases and indications, such as endogenous or anterior uveitis, corneal transplantation, Behcet's disease, vernal or ligneous keratoconjunctivitis, dry eye syndrome, and so forth. In addition, rejection of corneal allografts and stem cell grafts occurs in up to 90% of patients when associated with risk factors such as corneal neovascularization. CsA has been identified as a possibly useful drug for reducing the failure rate of such surgical procedures for those patients. Thus, other feasible delivery routes for such drugs that can avoid such drawbacks associated with systemic delivery are in demand.

Apart from implant therapies, other local administration routes for the eye have included topical delivery, such as ophthalmic drops and topical ointments containing the medicament. Tight junctions between corneal epithelial cells limit the intraocular penetration of eye drops and ointments. Topical delivery to the eye surface via solutions or ointments can in certain cases achieve limited, variable penetration of the anterior chamber of the eye. However, therapeutic levels of the drug are not achieved and sustained in the middle or back portions of the eye. This is a major drawback, as the back (posterior) chamber of the eye is a frequent site of inflammation or otherwise the site of action where, ideally, ocular drug therapy should be targeted for many indications.

Age-related macular degeneration (AMD) is a common disease associated with aging that gradually impairs sharp, central vision. There are two common forms of AMD: dry AMD and wet AMD. About ninety percent of the cases of AMD are the dry form, caused by aging and thinning of the tissues of the macula; a region in the center of the retina that allows people to see straight ahead and to make out fine details. Although only about ten percent of people with AMD have the wet form, it poses a much greater threat to vision. With the wet form of the disease, rapidly growing abnormal blood vessels known as choroidal neovascular membranes (CNVM) develop beneath the macula, leaking fluid and blood that destroy light sensing cells and causing a blinding scar tissue, with resultant severe loss of central vision. Wet AMD is the leading cause of legal blindness in the United States for people aged sixty-five or more with approximately 25,000 new cases diagnosed each year in the Unites States. Ideally, treatments of the indication would include inducing an inhibitory effect on the choroidal neovascularization (CNV) associated with AMD. However, in that the macula is located at the back of the eye, treatment of CNVM by topical delivery of pharmacological agents to the macula tissues is not possible. Laser photocoagulation, photodynamic therapy, and surgical removal is currently used to treat CNVM. Unfortunately, the recurrence rate using such methods exceeds 50% within a year of therapy.

As an approach for circumventing the barriers encountered by local topical delivery, local therapy route for the eye has involved direct intravitreal injection of a treatment drug through the sclera (i.e., the spherical, collagen-rich outer covering of the eye). However, the intravitreal injection delivery route tends to result in a short half life and rapid clearance, without sustained release capability being attained. Consequently, daily injections are frequently required to maintain therapeutic ocular drug levels, which is not practical for many patients.

Given these drawbacks, the use of implant devices placed in or adjacent to the eye tissues to deliver therapeutic drugs thereto should offer a great many advantages and opportunities over the rival therapy routes. Despite the variety of ocular implant devices which have been described and used in the past, the full potential of the therapy route has not been realized. Among other things, prior ocular implant devices deliver the drug to the eye tissues via a single mode of administration for a given treatment, such as via slow constant rate infusion at low dosage. However, in many different clinical situations, such as with CNVM in AMD, this mode of drug administration might be a sub-optimal ocular therapy regimen.

Another problem exists with previous ocular implants, from a construction standpoint, insofar as preparation techniques thereof have relied on covering the drug pellet or core with a permeable polymer by multi-wet coating and drying approaches. Such wet coating approaches can raise product quality control issues such as an increased risk of delamination of the thinly applied coatings during subsequent dippings, as well as thickness variability of the polymer around the drug pellets obtained during hardening. Additionally, increased production costs and time from higher rejection rates and labor and an increased potential for device contamination from additional handling are known problems with present implant technology.

Accordingly, this invention provides local treatment of a variety of eye diseases. The present invention also provides a method for the delivery of pharmaceuticals to the eye to effectively treat eye disease, while reducing or eliminating the systemic side effects of these drugs. This invention also provides sustained-release ocular implants for administration of therapeutic agents to the eye for prolonged periods of time. Additionally, this invention provides multi-modal sustained-release ocular implants. The invention also provides methods for making ocular implants with reduced product variability. The invention also provides methods for making ocular implants well-suited for ocular treatment trials using animal models. Other advantages and benefits of the present invention will be apparent from consideration of the present specification.

SUMMARY OF THE INVENTION

The present invention provides ocular implant devices for the delivery of a therapeutic agent to an eye in a controlled manner. The invention also includes fabrication and implementation techniques associated with the unique ocular implant devices that are presented herein.

In one embodiment of this invention, ocular implants are provided which administer a therapeutic drug to the eye according to dual mode release kinetics during a single treatment regimen. For instance, an ocular implant under this embodiment of this invention delivers drug continuously to the eye by initial delivery at a high release rate to eye tissues soon after placement of the implant in or near the eye, as a first administration mode, followed by drug delivery via a continuous, sustained lower release rate thereafter, as a second administration mode, and within the same treatment regimen using the same implant device. The delivery of drug is never interrupted during the regimen, as a smooth transition occurs in the changeover from the high to low release rate modes of drug delivery during the regimen. In this manner, the delivery of drug by the implant is dual mode or dual action in nature. Animal model studies have been performed, which are described elsewhere herein, that confirm this dual mode performance capability in local eye therapies for several embodiments of implants of this invention. As a consequence, no intervention is needed between initiation of the treatment, i.e., installing the ocular implant, and discontinuation of the treatment regimen, i.e., exhaustion of the drug reservoir after a prolonged period of time.

Although not desiring to be bound to any particular theory, a large initial dosage is delivered at a relatively high release rate to the eye tissues via an ocular implant according to one embodiment of the present invention in a manner effective to substantially saturate the eye compartments, permitting an ensuing lower release rate, maintenance dosage delivered over a period of time by the same implant to more effectively reach the target site of treatment, even if located in a posterior chamber of the eye. A dual mode implant according to the embodiment of this invention provides the sustained-release of the therapeutic agent for a prolonged period of time after the period of high release kinetics.

For purposes of this application, the term 'loading dose' refers to a rapid release phase of a pharmacological drug in a mammalian organism in which an initial high release rate of the drug is observed followed by exponential or nearly exponential decline or decay in the release rate as a function of time. The terminology 'sustained dose' refers to the phase during which release rates are substantially constant over a prolonged period of time, and consequently concentration of the therapeutic agent in the eye tissues achieves a substantially steady state value over that period of time. The terms 'loading dose' and 'sustained dose' are used in connection with drug treatments of the eye, unless indicated otherwise. Moreover, from a pharmacological standpoint, the initial dosage delivered at a relatively high release rate constitutes a loading dose, and the sustained lower release rate dose constitutes a maintenance dosage, suitable for the effective treatment of an eye disease, disorder, ailment or condition. The terms "dose" and "dosage" are used interchangeably herein.

The present invention embodies implants which can provide such dual mode ("dual action") performance, or optionally other modes of therapy via modified configurations thereof which are also described herein.

One aspect of the invention relates to "matrix" type implants, so referenced occasionally herein for convenience sake as every embodiment of implant under this category at least includes a composite matrix of polymer and therapeutic agent dispersed therein.

In one embodiment of this aspect of the invention, an implant provides therapeutic agent to the eye, in which the implant includes:

(a) a composite material matrix layer including:
   (i) a therapeutic agent, and
   (ii) a polymeric matrix material into which the therapeutic agent is dispersed, including (1) a polymer permeable to the therapeutic agent and present as a bioerodible solid matrix structure, and (2) a water-soluble polymer having greater water solubility than the permeable polymer, and (b) optionally, a discrete solid core containing additional therapeutic agent, which is surrounded and covered by the composite material matrix layer.

This matrix type implant configuration is particularly well-suited for subconjunctival or intravitreal placement, but is not limited thereto and could be installed on or in other eye regions where convenient and useful.

In a more specific embodiment, the composite material matrix layer component of the matrix type implant comprises about 5 to about 50 wt % permeable polymer, about 0.05 to about 90 wt % water-soluble polymer, and about 1 to about 50 wt % therapeutic agent. Preferably, the composite material matrix layer component comprises about 5 to about 20 wt % permeable polymer, about 0.05 to about 20 wt % water-soluble polymer, and about 1 to about 50 wt % therapeutic agent. As fabricated, the implant is a solid structure.

In one preferred embodiment of the matrix type implant, the permeable polymer is a superhydrolyzed polyvinyl alcohol (PVA), which permits diffusion of the therapeutic agent therethrough, and forms a slowly bioerodible solid structure, and the water-soluble polymer is a pharmaceutical grade cellulose ether. Uncrosslinked superhydrolyzed PVA releases the drug by surface erosion of the PVA and by diffusion of the drug through the superhydrolyzed PVA. The rate of erosion of the superhydrolyzed PVA is sufficiently slow that the polymer material in the implant will dissolve so that the therapeutic agent pellet ("drug pellet"), when included, will disintegrate only after an extended period of time, such as months or even years, in order to provide a slow sustained delivery of drug.

In addition, the superhydrolyzed PVA is water permeable and permeable to the therapeutic agent in a predictable manner upon saturation with body fluids, yet offers the advantage of undergoing very limited expansion when the implant is installed. The low wet expansion behavior of superhydrolyzed PVA prevents the implant from being extruded, and also permits more predictable pharmacokinetic behavior of the device. Also, the superhydrolyzed polyvinyl alcohol used in the polymeric matrix material is essentially noncrosslinked through its secondary hydroxyl functionality, i.e., it is not heated to temperatures during preparation of the implant sufficient to induce a level of crosslinking which impairs its permeability to the therapeutic agent present in either the inner core or the composite material matrix layer. The superhydrolyzed PVA is slowly bioerodible and not rapidly water-soluble in body fluids, so that the inner core does not disintegrate soon after installation of the implant. For purposes of this invention, a superhydrolyzed polyvinyl alcohol is a polyvinyl alcohol having at least 98.8 wt % hydrolysis, preferably at least 99.0 wt % hydrolysis, and most preferably at least 99.3 wt % or more hydrolysis. Generally, the superhydrolyzed polyvinyl alcohol for use in this invention generally have a weight average molecular weight of about 85,000 to about 150,000, and preferably about 100,000 to about 145,000.

On the other hand, the separate water-soluble polymer included in the polymeric matrix material provided in the matrix type implant preferably is a nonionic cellulose ether polymer. The cellulose ether polymer used generally has a weight average molecule weight of about 70,000 to about 100,000, and preferably about 80,000 to about 90,000. The water-soluble polymer is used as a processing aid during preparation of the composite material matrix layer. Namely, it acts as a suspension and dispersion aid for introducing the therapeutic agent into an aqueous medium, and before admixture with the superhydrolyzed PVA ingredient, in a premix step involved with fabricating the implant (discussed in more detail below). Examples of such cellulose ether compounds include hydroxyalkyl cellulose materials, such as hydroxypropyl methyl cellulose (HPMC), hydroxypropyl cellulose (HPC), and hydroxyethyl cellulose (HEC). In general, the higher the proportion of cellulose ether present in the polymeric matrix part of the matrix implant relative to the proportion of superhydrolyzed PVA, the more rapid the release of the therapeutic agent.

In one preferred embodiment of the matrix implant, a therapeutic agent is included in both the inner core or pellet and the exterior composite material matrix layer or cladding. This results in a dual mode release of the therapeutic agent or drug into the eye during a treatment regimen. That is, a loading dose is initially delivered to the eye by the matrix implant followed by a transition in the release rate, continuing uninterrupted drug delivery by the implant, down to a relatively steady maintenance dosage that is sustained over a prolonged period. Initially, the therapeutic agent is released both from the polymer matrix and the inner core or pellet of this embodiment of implant, creating the rapid release rate of the loading dose. Once the concentration of drug initially preloaded into the composite drug/polymer matrix cladding material diffuses into the eye, the maintenance dosage of drug is derived at a relatively constant rate from the remainder of the drug diffusing from the inner core or pellet through the composite material matrix layer which surrounds the core.

Moreover, an added advantage of this embodiment is that this dual mode therapy can be achieved via subconjunctival implant placement for some eye treatments. Thus, a less invasive and simpler procedure that does not require piercing of the vitreous body is provided. Used as a subconjunctival implant, it can be placed behind the surface epithelium within the subconjunctival space. It also is possible to install these implants at or near other specific sites on or within the eye, such as intravitreal, if desired or useful.

This matrix implant embodiment of the invention also can be deployed for single mode or single action therapy in the eye by omitting the solid core or pellet of therapeutic agent, and using the composite material matrix layer alone, which is the same general construction as that used in the dual mode device. The single mode matrix implant releases a loading dose for a short period of time (e.g., up to about 30 days), but does not provide a sustained maintenance dosage over a prolonged period thereafter.

In an optional configuration, a portion of the outer surfaces of the matrix implant, such as one side of the composite material matrix layer, has a top coat provided that is a polymeric material that is impermeable to the therapeutic agent, such as polymethyl methacrylate (PMMA). In this way, the release rate of the matrix implant can be reduced in a managed manner, if desired.

As another alternative embodiment of matrix implant according to this invention, poly(ethylene vinyl) acetate (EVA) control can be used in the polymeric matrix material in lieu of the superhydrolyzed PVA. EVA is nonbiodegradable and permeable to water. In the same general manner as the PVA-based matrix implants, the EVA-based matrix implants can provide dual mode or single mode drug release depending on whether the drug pellet is included (dual mode, i.e., loading plus slow constant rate release) or not (single mode, i.e. slow constant rate release only).

Both the dual mode and single mode variants of the matrix implants of this invention are well-tolerated and non-toxic to the patient or recipient (i.e., a mammalian host—human or veterinary). In addition, the matrix implant design of this invention can be prepared by unique methodologies and selections of materials leading to and imparting the unique pharmacological performance properties present in the finished devices.

Among other eye therapies, the matrix implant of the present invention, such as when used in a subconjunctival placement, provides an effective treatment in corneal transplantation procedures to reduce rejection rates. For example, an immune system modifier agent such as cyclosporine can be delivered non-systemically to the eye, in order to reduce rejection rates of corneal allografts. Alternatively, this implant can be installed in the vitreous humor to deliver 2-methoxyestradiol (occasionally abbreviated herein as "2ME2") for treatment of CNVM. Also, other drugs or drug cocktails can be delivered as desired and appropriate.

Another aspect of the invention relates to "reservoir" type implants which include a silicone-encapsulated reservoir containing therapeutic agent. The reservoir type implants of this invention are intraocular, and preferably intravitreous implants. The intraocular reservoir implants are sustained-release devices which deliver therapeutic agent to the eye over a prolonged period of time.

The intraocular reservoir implant generally includes an inner core comprising a therapeutic agent for the eye covered by, and radially centered within, a polymeric layer comprising a nondegradable material permeable to the therapeutic agent, as a subassembly, and an ocular attachment means affixed to an exterior surface of the polymeric layer of the subassembly. In a preferred embodiment of the invention, the nondegradable material is silicone.

Methodologies are used in this intraocular reservoir implant configuration which ensure that the silicone is degassed and that the inner core is well-centered, at least radially, within a polymer comprising silicone. This results in unhindered diffusion of the drug from the reservoir through the silicone, as air bubbles or pockets are eliminated which otherwise would not permit such diffusion. As a result, a controlled and predictable drug release rate can be obtained. Centrifugation is used in conjunction with a temporary thin walled tubular mold made of low adhesion plastic in a multi-step process effective to degas the silicone encapsulating material and radially center the drug core within a polymeric material before the polymeric material is fully hardened.

In one embodiment of preparing the intraocular reservoir implant, the steps of the method generally include positioning a thin walled tube made of low adhesion (releasable) plastic, such as a polytetrafluoroethylene tube, in a temporarily fixed upright position within a centrifuge tube. A base made of hardened silicone, or a polymeric material having similar permeability, is then formed at the bottom section of the plastic tube, such as by introducing a curable silicone fluid in the bottom of the microcentrifuge tube, positioning a bottom section of plastic tube below the surface of the curable silicone fluid. This is done in a manner such that the silicone fluid infiltrates and fills a lower section of the plastic tube, and also fills the space between the outer surface of the lower section of the plastic tube and the inner facing wall of the centrifuge tube, followed by curing or hardening the silicone fluid to hold the plastic tube in an upright position within the microcentrifuge tube. Thereafter, a drug pellet, as the drug core, is introduced into the plastic tube followed by addition of additional wet silicone into the plastic tube. The microcentrifuge tube is centrifuged as needed to degas the additional silicone and place, if necessary, the pellet on the silicone base positioned at the bottom of the plastic tubing. The additional curable silicone fluid added inside the plastic tube is sufficient to completely immerse the exposed surfaces of the pellet as it rests on the hardened silicone base. As needed, the drug pellet can be manually or mechanically centered on the silicone base using an insertable/retractable device or probe to move and center the pellet as needed. The added silicone fluid is then cured inside the plastic tube. After the silicone is cured, the plastic tube is separated from the centrifuge tube, and the resulting silicone-coated pellet reservoir type implant is in turn removed from the releasable plastic tube, as an implant subassembly. The reservoir implant subassembly is joined to a means for attaching the implant subassembly to intraocular tissues of the eye, such as a suture stub.

As an alternative to the suture stub, a silk mesh fabric can be embedded in the silicone at one end of the reservoir type implant. This allows a suture to pass through the mesh embedded at the one end and the suture will not scissor through the soft silicone since it is caught by the mesh. The suture then passes through the edges of the scleral wound and is tied down.

The implant subassembly of the intraocular reservoir implants of the invention provide a sustained, substantially constant delivery rate of drug over a prolonged period. The intraocular reservoir implants also can be modified to form dual mode release devices. For instance, in a dual mode configuration, additional therapeutic agent could be dispersed in the silicone fluid before being used to encapsulate the drug core to create an initial higher release rate, or loading dose; alternatively, additional amounts of the drug could be dispersed in or attached as a discrete inlay member onto a separate silicone adhesive used to attach a surface of the reservoir implant subassembly to a suture stub or the like. Alternatively, multi-drug therapy could be provided by including a drug different from the drug core in the silicone surrounding the pellet or, in or on the silicone adhesive used to affix the implant reservoir subassembly to the suture stub. In another embodiment, more than one reservoir implant subassembly, each comprising an encapsulated drug core, can be attached to a common suture stub to provide concurrent delivery of different drugs or additive introduction of a common drug.

As another dual mode embodiment of the reservoir implant, a circular wafer shaped pellet or tablet of therapeutic agent having a larger radial diameter than thickness can be fixed to a suture stub with silicone adhesive; and a temperature-curable type silicone adhesive is then used to form a coating bead around the periphery of the wafer-shaped pellet or tablet. Curing the bead of silicone coating around the tablet periphery can be delayed (preferably for about 18 to 30 hours, more preferably approximately 24 hours), by keeping the coated assembly at room temperature (e.g., 20–30° C.); thereafter peripheral bead coating of silicone ultimately becomes fully cured. The silicone adhesive is in a constant state of curing but the process is not complete for 18–30 hours. The top surface of the tablet is coated separately with silicone before or after this "delay in cure" procedure, and cured. During the interim delay in cure period, some, but not all, of the therapeutic agent diffuses into the surrounding nonfully cured silicone coating polymer at its periphery, which creates a high release rate or loading dose when the implant is initially installed, followed by slow, lower dosage sustained release of the therapeutic agent.

Among other eye therapies, the intraocular reservoir implants of the present invention provide an effective treatment for sight-threatening eye diseases that include but are not limited to uveitis, age-related macular degeneration, and glaucoma. Therapeutic agents useful in this implant design include, for example, 2-methoxyestradiol (2ME2) or angiogenesis compounds such as VEGF antagonists for treating CNVM; or corticosteroids for treating uveitis, to name just a few examples.

The therapeutic agents and drugs deliverable by the implants of this invention generally are low solubility substances relative to the various polymeric matrices described herein, such that the agents diffuse from the drug core into and through the polymer material, when saturated with body fluids, in a continuous, controlled manner.

The therapeutic agents and drugs that can be delivered by the implants of this invention include, for example, antibiotic agents, antibacterial agents, antiviral agents, anti-glaucoma agents, antiallergenic agents, anti-inflammatory agents, anti-angiogenesis compounds, antiproliferative agents, immune system modifying agents, anti-cancer agents, antisense agents, antimycotic agents, miotic agents, anticholinesterase agents, mydriatic agents, differentiation modulator agents, sympathomimetic agents, anaesthetic agents, vasoconstrictive agents, vasodilatory agents, decongestants, cell transport/mobility impending agents, polypeptides and protein agents, polycations, polyanions, steroidal agents, carbonic anhydride inhibitor agents, and lubricating agents, and the like singly or in combinations thereof.

In these and other ways described below, the inventive implants offer a myriad of advantages, improvements, benefits, and therapeutic opportunities. The inventive implants are highly versatile and can be tailored to enhance the delivery regimen both in terms of administration mode (s) and type(s) of drugs delivered. The implants of this invention permit continuous release of therapeutic agents into the eye over a specified period of time, which can be weeks, months, or even years as desired. As another advantage, the inventive implant systems of this invention require intervention only for initiation and termination of the therapy (i.e., removal of the implant). Patient compliance issues during a regimen are eliminated. The time-dependent delivery of one or more drugs to the eye by this invention makes it possible to maximize the pharmacological and physiological effects of the eye treatment. The inventive implants have human and veterinary applicability.

BRIEF DESCRIPTION OF THE DRAWINGS

Other features, benefits, and advantages of the present invention will become apparent from the following detail description of preferred embodiments of the invention with reference to the drawings.

FIGS. 8A–I schematically depicts an enlarged view of process steps associated with making a reservoir implant subassembly according to another embodiment of this invention.

FIG. 16 is a table of the 2ME2 in vitro release rates observed for the intravitreal reservoir dual mode implant studies described in Example 6 herein.

Figure 1:
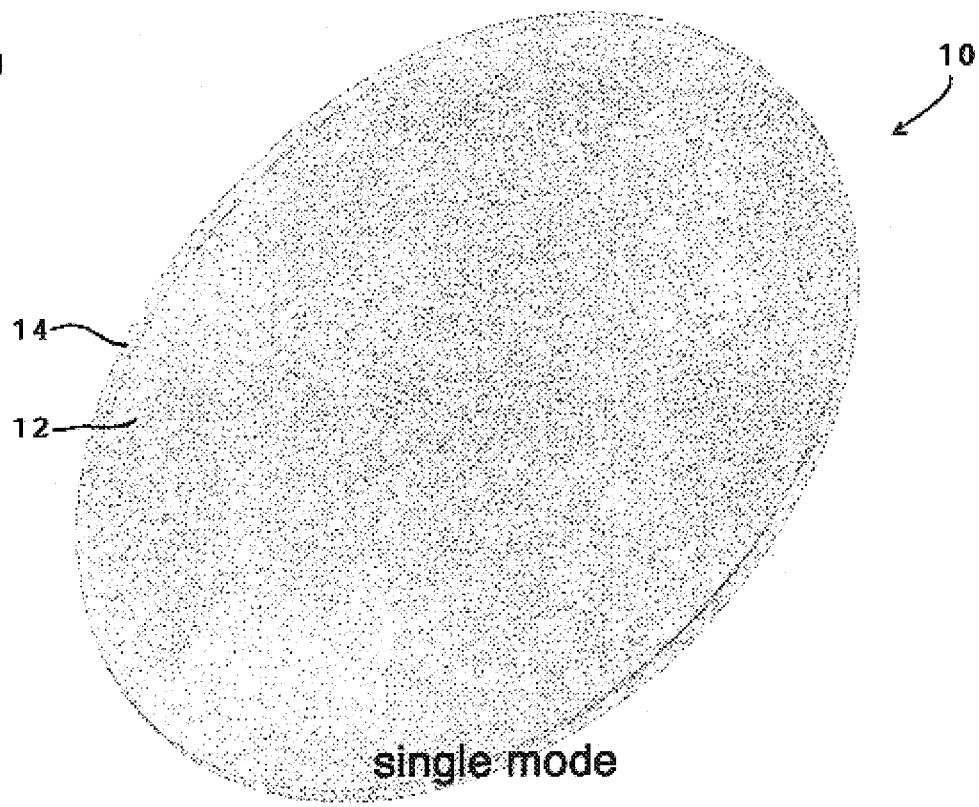
FIG. 1 is enlarged view of a sustained release, subconjunctival matrix single mode implant device according to an embodiment of the invention.

Skilled artisans will appreciate that elements in the figures are illustrated for simplicity and clarity and have not necessarily been drawn to scale. For example, the dimensions of some of the features shown in the figures may be enlarged relative to other elements to better illustrate and/or facilitate the discussion herein of the embodiments of the invention. Features in the various figures identified with the same reference numerals represent like features, unless indicated otherwise.

DETAILED DESCRIPTION OF THE INVENTION

Matrix Implants:

Referring now to the figures, and in particular to FIG. 1, a sustained release, matrix single mode implant device 10 of the invention is shown comprised of a single composite material matrix layer containing a dispersion of a therapeutic agent, seen as white particles 12 in the figure, and a polymeric matrix material 14 into which the therapeutic agent is dispersed. The polymeric matrix includes a polymer permeable to the therapeutic agent and present as a bioerodible solid matrix structure, and a water-soluble polymer having greater water solubility than the permeable polymer.

This implant configuration provides a single-mode, single action therapy in the eye in which a loading dose of drug is released.

Figure 2A:
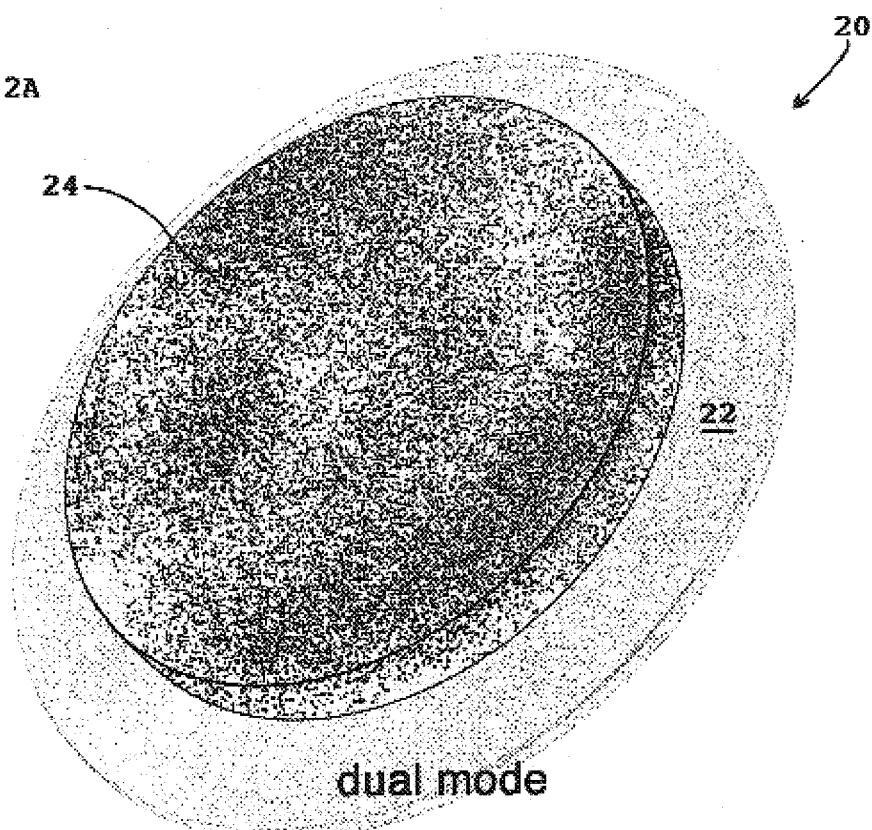
FIG. 2A is enlarged view of a sustained release, subconjunctival matrix dual mode implant device according to an embodiment of the invention, in which a drug pellet is surrounded by a composite material matrix layer including polymeric material and a dispersion therein of additional drug.
Figure 2B:
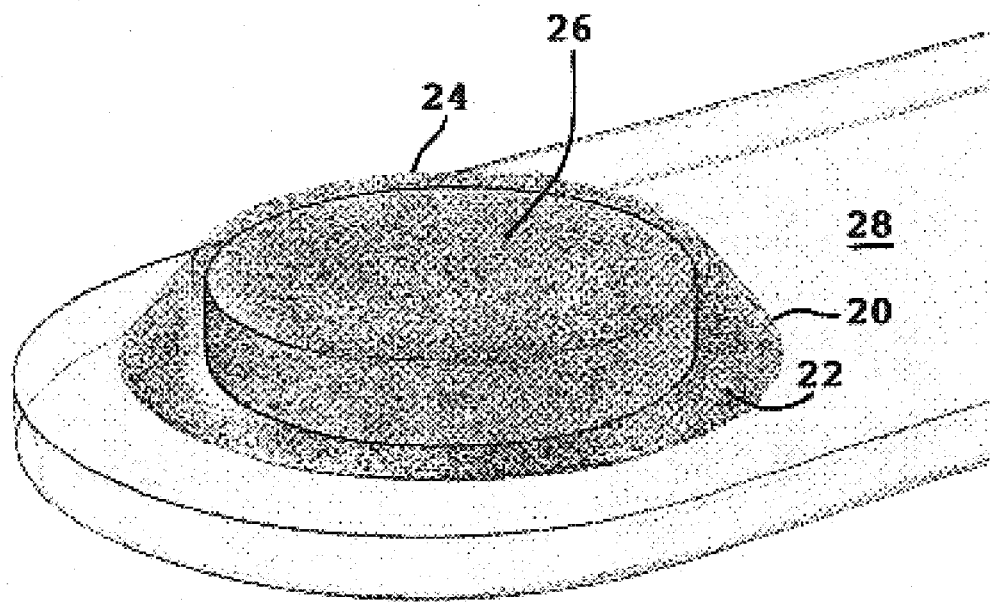
FIG. 2B is a view of the sustained release, subconjunctival matrix dual mode implant device similar to the one shown in FIG. 2A, including a view of the drug pellet surrounded by the polymeric material and dispersed additional drug, and an optional eye attachment (suture stub). The cross-section shows the relationship of the drug pellet to the surrounding polymer coating.

Referring now to FIG. 2A, a modified variant of the matrix implant shown in FIG. 1, is illustrated, which provides dual mode (dual action) drug delivery to an eye. In this implant 20, a drug core or pellet embedded and encapsulated within a composite material matrix layer 22, 24 having the composition described above for implant 10. The composite material matrix layer includes a flat base portion 22 upon which the bottom of the drug pellet rests, and an upraised portion 24 which conformably makes intimate physical contact with the top and side surfaces of the drug pellet. The drug pellet 26 is not visible in FIG. 2A. FIG. 2B illustrates the embedded drug pellet 26, and an optional suture stub 28 that can be used to attach the implant 20 to eye or other nearby tissue if desired or useful.

Figure 3A:
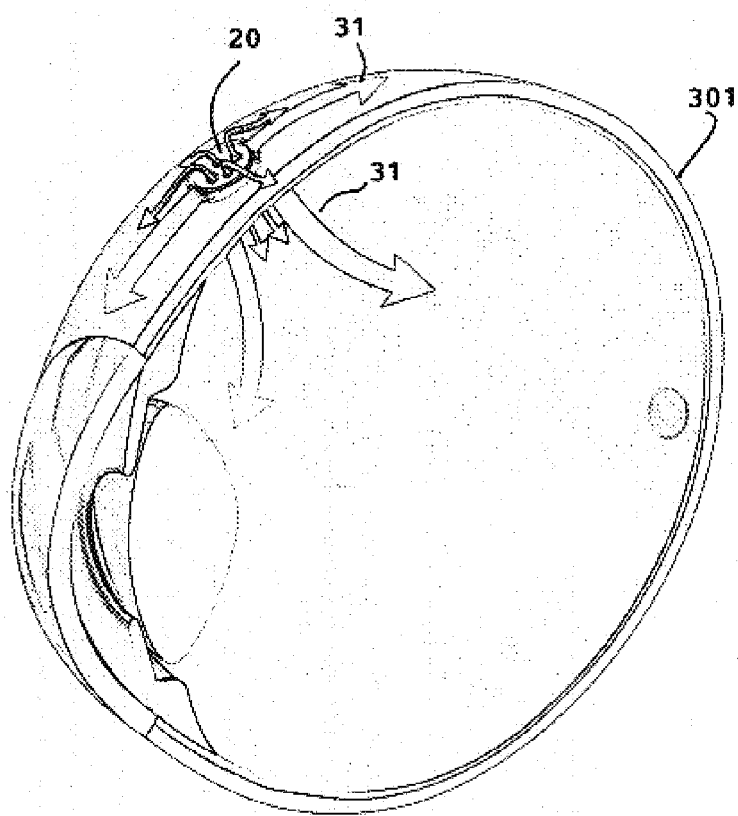
FIG. 3A schematically illustrates the delivery of a loading dose by a subconjunctival matrix dual mode implant of this invention into the surrounding tissues and vitreous cavity.
Figure 3B:
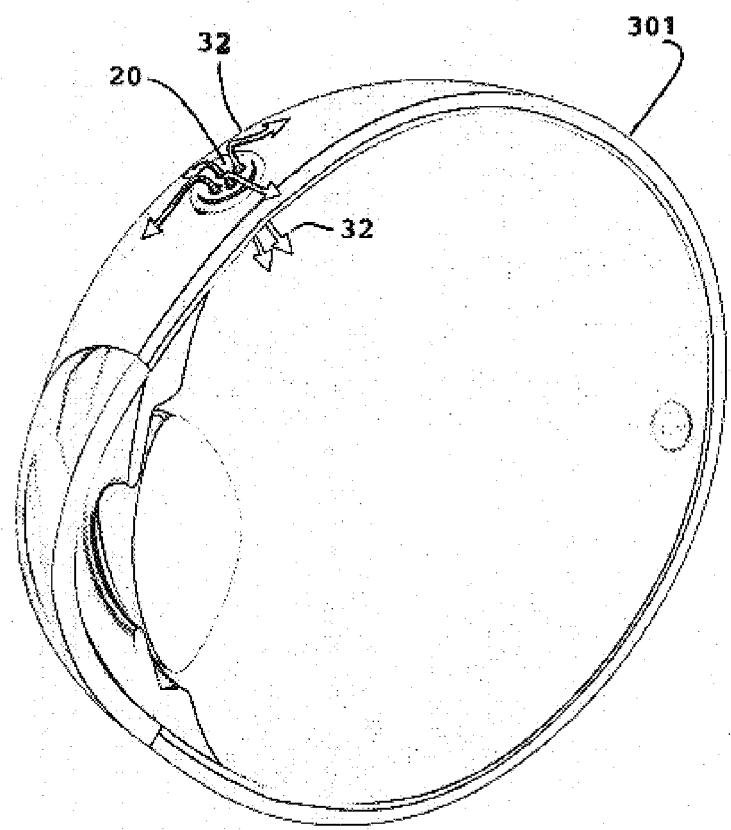
FIG. 3B schematically illustrates delivery of a maintenance dosage by the subconjunctival matrix dual mode implant shown in FIG. 3A, subsequent to delivery of the loading dose.

In this way, and as illustrated in FIGS. 3A and 3B, therapeutic agent is included in both an inner core or drug reservoir and as dispersed in the exterior composite material matrix layer or cladding of implant 20. This results in dual mode or bimodal release of the therapeutic agent into the eye 301 during a treatment regimen. That is, a loading dosage is initially delivered by the conjunctival implant (FIG. 3A), followed by a transition in the release rate, during continuing uninterrupted drug delivery by the implant, down to a relatively steady lower maintenance dosage 32 that is sustained over a prolonged period (FIG. 3B).

Figure 4A:
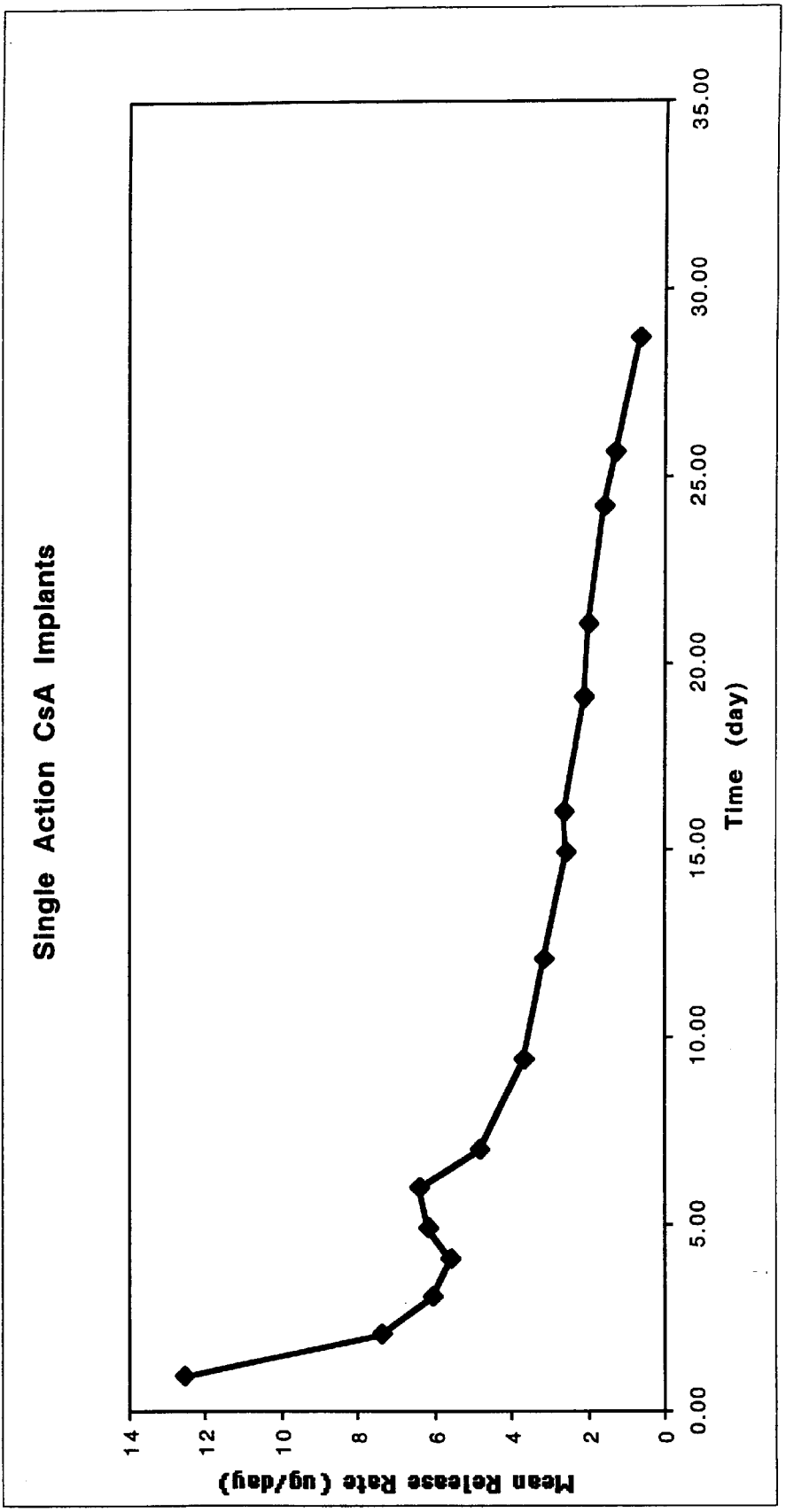
FIG. 4A graphically illustrates the delivery of a delivery of a loading dosage according to a subconjunctival matrix single mode implant of this invention described in Example 4 herein.
Figure 4B:
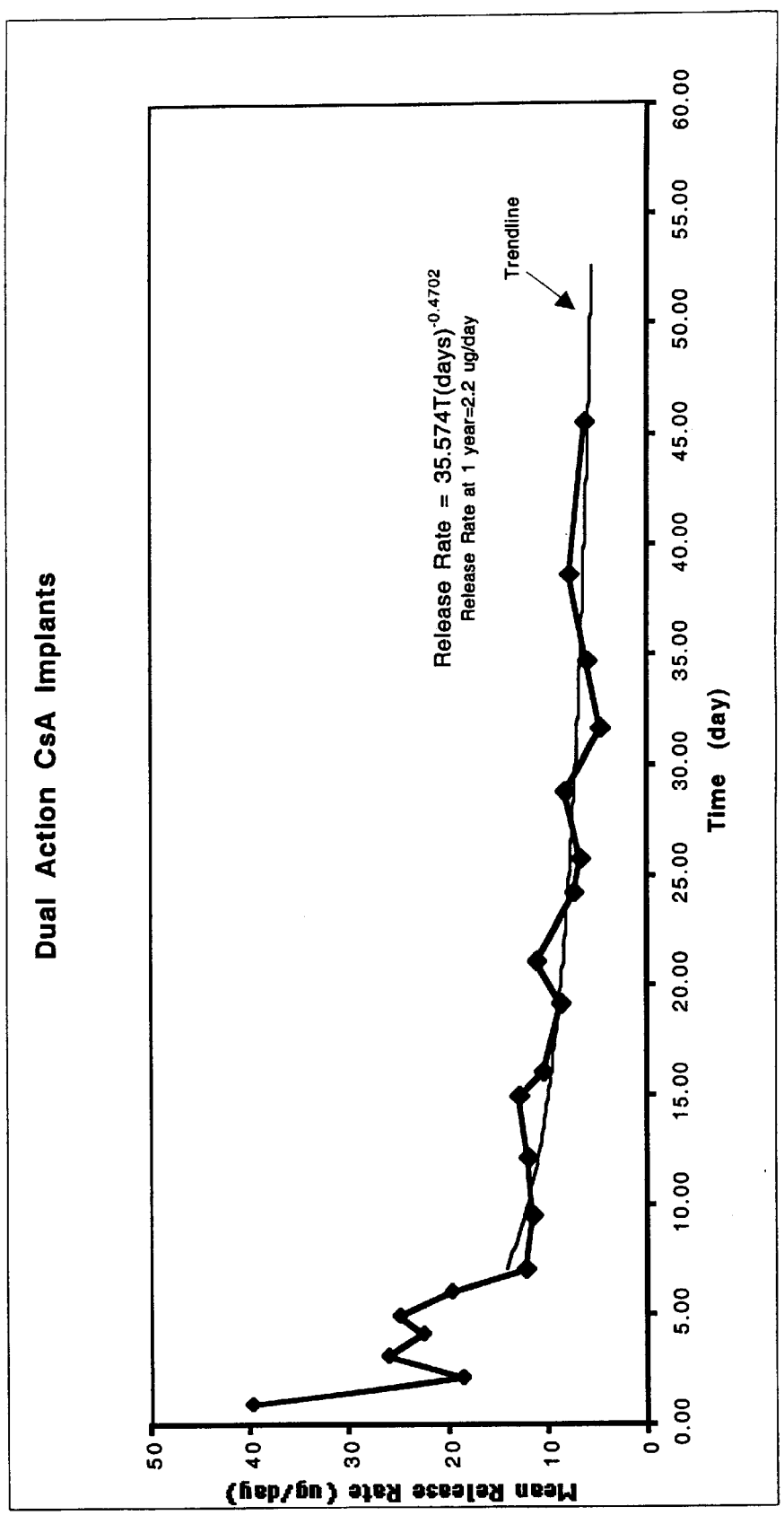
FIG. 4B graphically illustrates the delivery of a loading and maintenance dosage according to a subconjunctival matrix dual mode implant of this invention described in Example 4 herein.

FIGS. 4A–B, based on data developed in the studies described in Example 4 infra, graphically show the difference in the single mode matrix implant (FIG. 1) performance as compared to that of the dual mode matrix implant (FIG. 2A) which further includes a drug pellet core.

For the dual mode matrix implant, the therapeutic agent initially is released both from the polymer matrix and the inner core reservoir of this embodiment of the subconjunctival implant, creating the loading dosage. Once the concentration of drug initially preloaded into the composite cladding material diffuses out into the eye, the maintenance dosage of drug is derived at a relatively constant rate from the remainder of the drug diffusing from the inner core through the composite material.

As to the materials used in constructing the matrix implants, the following considerations are important. The composite material matrix layer or member (22, 24) includes at least, and preferably predominantly or exclusively, the following three ingredients: (1) a drug permeable polymer, (2) a water soluble polymer, and (3) a dispersed therapeutic agent.

The permeable polymer preferably is superhydrolyzed polyvinyl alcohol. The permeable polymer is imperforate; i.e., it is not microporous. Thus, the drug or therapeutic agent passes through it by diffusion process. For purposes of this invention, a superhydrolyzed polyvinyl alcohol means a polyvinyl alcohol of at least 98.8 wt % hydrolysis, preferably at least 99.0 wt % hydrolysis, and more preferably 99.3 wt % or more hydrolysis. Superhydrolyzed PVA is obtained in granular powder form from Air Products and Chemicals, Inc., Allentown, Pa., U.S.A., as Airvol 125. Airvol 125 has at least 99.3 wt % hydrolysis, and intermediate viscosities of 28–32 cps and a pH of 5.5–7.5. The superhydrolyzed PVA that can be used in this invention generally has a weight average molecular weight of about 85,000–150,000, and preferably about 100,000 to about 145,000. Additional information on superhydrolyzed PVA is provided at CAS No. 900289-5. Other suitable superhydrolyzed PVA products, include Airvol 165, also available from Air Products and Chemicals, Inc., Allentown, Pa., U.S.A.

Superhydrolyzed PVA provides the requisite functionalities of permitting diffusion of the therapeutic agent while forming a slowly bioerodible structure in the composite material matrix layer or member (22, 24) of the implant. The rate of erosion of the superhydrolyzed PVA is sufficiently slow that a slow sustained delivery of drug, such as many months or even years, can be obtained as desired.

In addition, the low wet expansion behavior of superhydrolyzed PVA prevents the implant from being extruded from its position within or near the eye, and also permits more predictable pharmacokinetic modeling behavior of the device. For example, once the subconjunctival matrix implants of this invention are implanted in the subconjunctival space (e.g., in a rabbit), after 3–4 weeks, the edges of the matrix implants constructed with superhydrolyzed PVA have been observed to soften as the surface of the polymer hydrates which decreases the risk that it will extrude (i.e., a sharp edge under the conjunctiva tends to catch the lid when it blinks, and this would undesirably move the implant anteriorly and increase the risk it will extrude at the corneal limbus). Also, the superhydrolyzed PVA totally conforms to the globe of the eye and is adherent to the sclera after 3–4 weeks.

For bulkier implants (e.g. dual mode implants with large drug pellets) that are at higher risk of extrusion, one or two sutures can be placed through the edges of the implant to secure the implant to the sclera.

Also, the superhydrolyzed polyvinyl alcohol used in the polymeric matrix is essentially noncrosslinked through its secondary hydroxyl functionality, i.e., it is not heated to temperatures during preparation of the implant sufficient to induce a level of crosslinking which impairs its permeability to the therapeutic agent present in either the inner core or the composite matrix material.

Heating the matrix implants at temperatures >100° C. for 3–8 hours will encourage PVA crosslinking and this may be desirable when attempting to reduce drug release rates from a particular implant.

The separate water-soluble polymer included in the polymeric matrix material is a nonionic cellulose ether. Among other things, acts as a suspension and dispersion aid for the therapeutic agent in premix step involved with fabricating the implant. Examples of such cellulose ether include hydroxyalkyl cellulose materials, such as hydroxypropyl methyl cellulose (HPMC), hydroxypropyl cellulose (HPC), and methylcellulose (MC). HPMC can be obtained as METHOCEL from Dow Chemical (e.g., METHOCEL E4M). METHOCEL is cellulosic in nature. It is dissolvable in the same temperature ranges as superhydrolyzed PVA. The preferred hydroxypropyl methyl cellulose has a weight average molecular weight of about 70,000 to about 100,000, preferably about 80,000 to about 90,000, and more preferably about 85,000.

In that many useful therapeutic agents for ocular treatments are hydrophobic or lipophilic in nature, the present invention provides a processing strategy effective to uniformly disperse and maintain a suspension of such active agents and compounds in an aqueous medium in the preparation of the matrix implants. To accomplish this, the method for preparing the composite material matrix layer component of the matrix implants includes a step of separately mixing and dispersing the therapeutic agent to be incorporated in the composite (cladding) material first with cellulose ether and the like, which acts as a dispersing or emulsifying aid to permit an emulsion-like suspension of therapeutic agent in an aqueous fluid. Generally, this premixture will involve preparing an aqueous emulsion or suspension containing a mixture of drug and an amount of cellulose ether effective to provide the abovementioned processing aid effects needed. This preliminary dispersion and suspension of the therapeutic agent using the cellulose ether is done in the absence of the superhydrolyzed PVA and without heating. The premixture generally comprises the drug in a range amount of about 1.5% to about 80% and the cellulose ether in a range amount of about 0.05% to about 95%, on a dry weight basis.

In general, the premixture is not heated. An occasional drug needs 70–110° C. to help the dispersion of the drug in the premixture.

Thereafter, the separately prepared emulsion or suspension of drug and dispersing aid polymer then is combined and mixed effectively and thoroughly with an aqueous solution of the superhydrolyzed PVA ingredient. The superhydrolyzed PVA solution generally contains about 5 to about 50 wt % of the superhydrolyzed PVA. Higher concentration solutions of superhydrolyzed PVA are more difficult to work with due to increased viscosities. To optimize the drug suspension when using high concentrations of PVA, preferably small volumes are prepared of the PVA solution with frequent stirring under mild (noncrosslinking) heat.

The superhydrolyzed PVA solution can be combined with the cellulose ether/drug mixture with a spatula or other suitable manual mixing instruments. However, for more highly viscous suspensions, a blender may be desirable. As such a blender, a MiniContainer is adapted to the blender to hold small volumes, where the blender is a Laboratory Blender (Model 51BL30), operated at speeds of 18,000 RPM (low) or 22,000 RPM (high) as needed. The Mini Container (MMGC1) was stainless steel and held 12–37 ml, and was obtained from Waring Factory Service Center, Torrington, Conn. To add the materials to a blender, a bottom of the assay tube containing the PVA/METHOCEL/drug mixture is cut with a razor blade and the contents poured into the blender. In one method, the mixture is blended at high speed (22K RPM) for up to 5 minutes, and the blended contents are then poured into a 50 ml assay tube and centrifuge for 2 minutes at 1–4k RPM to degas it.

In this way, an overall homogenous premixture can be provided for the composite material matrix layer that includes the three abovementioned ingredients.

When describing the components of the PVA/cellulose ether/drug mixture, the PVA is expressed as a wt % of the PVA/water solution, e.g., 50 grams of PVA in 100 ml of water is a 50% PVA solution. However, the other components, i.e., the drug and cellulose ether, weights are expressed as the % of the total dry weight of the PVA/ cellulose ether/drug mixture. The combined drug/cellulose ether premixture and PVA solution generally has a composition of about 5 wt % to about 50 wt % superhydrolzyed PVA, about 0.05 wt % to about 90 wt % cellulose ether, about 1 to about 50 wt % drug. More preferably, the composite material matrix layer comprises about 5 to about 20 wt % superhydrolyzed PVA, about 0.05 to about 20 wt % cellulose ether, and about 1 to about 50 wt % therapeutic agent.

The homogenous premixture including the three above-mentioned ingredients, then is formed into a sheet-like coating on a flat releasable surface, or is injected between two releasable plates (e.g. glass) to provide a uniform desired thickness, and dried at room temperature and without application of heat (i.e., preferably at less than about 30° C.). Pieces of the dried uncrosslinked material are cut after drying from the sheet in the profiles desired for the matrix implant. At this point, a single-mode version of the implant (FIG. 1) has been manufactured. Other implant shapes, such as a curvilinear design, can be easily fabricated to conform to the curvature of the cornea, which may be helpful for corneal or stem-cell graft transplantation and ocular inflammatory diseases. The dried matrix implant is uncrosslinked so that it is bioerodible.

For lower concentrations of PVA in the composition of matrix implants, such as less than about 15 wt %, the homogenous drug/cellulose ether/PVA mixture can be poured out onto a glass plate and this will flatten out on its own upon drying without the need for compression via a top plate. Alternatively, the mixture can be compressed between two glass plates to further ensure uniform thickness. The top glass plate can be removed without damaging the drug/cellulose ether/PVA composite by cooling the lay-up before its removal. One glass plate (top one) is removed after cooling, and the other is left so that the PVA has a place to dry. The surface tension of the PVA generally keeps it adhered to the bottom glass plate so that it dries as a flat sheet. If both glass plates are removed simultaneously after the cooling step, the PVA curls up and is not usable. Where PVA concentrations higher than about 15% are used in making a matrix implant, such as about 50 wt % PVA, the sandwich or double glass plate technique preferably is used to help flatten out the surface of the coating before it dries.

For preparation of dual mode matrix implants (FIG. 2A), a modified process is required to introduce and embed the inner drug core. The drug core is a self-supporting solid or semi-solid part containing the drug, and has any convenient shape conducive for the making of sealing coverage thereon by the composite material. For instance, the core can be formed as a cylindrical-shaped pellet of the drug alone, or in combination with a pharmaceutically acceptable carrier. In any event, the dual-mode implant is assembled by depositing the drug core, such as drug pellet or tablet, on the surface of a freshly prepared and coated layer of the composite material while still semi-flowable; the pellet is then tapped or pushed with light force on its upper surface, such by use of an elongated tipped surgical device (e.g., a triple-0 Bowman probe), so as to submerge and embed it completely within and in contact with the polymeric coating layer; finally, the polymeric material is hardened or cured around the pellet (generally at room temperature) to fix it in position. The polymeric coating layer thickness is selected to adequate to permit complete encapsulation of the drug pellet. The submerging of the drug pellets into the wet, non-fully dried PVA slabs according to this invention avoids tendencies of alternate approaches involving multiple dip and dry coat applications that tend to delaminate in use, thereby dramatically altering the drug release rates. Also, when drug pellets are embedded in a matrix with high PVA concentrations to make dual mode implants, this preferably is done by embedding them at the edges where the two glass plates come together and the polymer is exposed.

As seen in FIG. 2A, when a drug pellet having a rounded tablet shape is used, the matrix implant resulting from drying the above-mentioned matrix coating layer containing the pellet has a saucer like shape with a flat surface on one side, and a hat shape on the opposite side, where the drug core is completely and physically intimately covered by a polymer coating including dispersed drug, without any entrapped air pockets or air spaces inside the implant. Depending on the type of mammal intended for treatment with this implant, the purpose of the ocular treatment, and the type of drug and polymer coating material, the drug pellet cores generally range in diameter from about 1 mm to about 5 mm and about 1.0 to about 2.5 mm in thickness, and the thickness of the polymeric coating can range from about 0.01 mm to 1.0 mm (as measured from a pellet surface to the outer surface of the polymeric layer). In the case of the single-mode matrix implants, the thickness of the homogenous wafer-shaped polymeric material generally ranges from about 0.1 mm to 2 mm, and the wafer has opposite flat surfaces.

Adjusting the loading dose in the matrix implant generally can be done by changing the relative proportions of superhydrolyzed PVA, cellulose ether, and drug in the matrix component. The maintenance dose delivered by the dual mode matrix implants can be adjusted by changing the surface area of release (i.e., generally by altering the geometry and mass of the compressed drug pellet).

For instance, for a more rapid release rate in the matrix implant, a higher proportion of the cellulose ether can be used relative to the proportion of superhydrolyzed PVA. If the mixture is predominantly cellulose ether, however, the loading dose generally lasts for only 24 hours maximum. In that situation, during fabrication of the implant, the pellet is precoated with 15% uncrosslinked PVA (e.g., Airvol 125) and dried, before the coated pellet is embedded within the wet polymeric coating slab. In this way, when the cellulose ether rapidly dissolves, the pellet still holds together.

Figure 5:
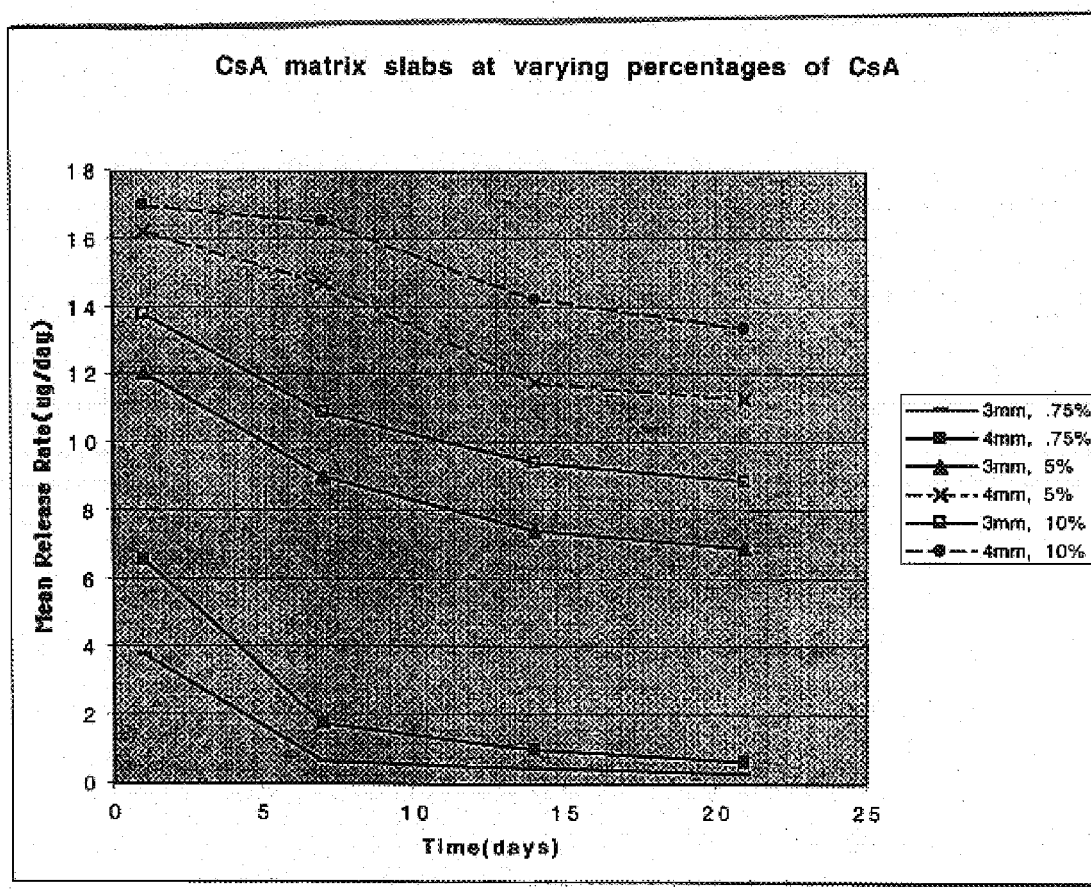
FIG. 5 graphically illustrates the effect of surface area and drug concentration on release rates for a subconjunctival matrix single mode implant of this invention.

Other than the mixing proportions of the ingredients, factors affecting the release rate in the matrix implants include: the permeability of the drug in the matrix polymers; the drug concentration in the laminate layer and in the embedded pellet; the surface area of the pellet; the amount of surface of the matrix polymeric layer disposed on the eye. The effect of the surface area and drug concentration on the release rates of single mode matrix implants can be seen in FIG. 5.

Also, a slightly modified superhydrolyzed PVA polymer can be used to modify the quantity and duration of the loading dose. For example, using progressively higher amounts of gamma radiation and/or heat exposure, can crosslink the PVA and reduce the implant release rate. Chemical curing agents or catalysts are generally not employed since the extent of cross-linking becomes to extensive and the loading dose drug release capability can be lost. If radiation, thermal or chemical crosslinking is too extensive, the PVA will have inadequate permeability to the drug for the implant to function effectively.

In another embodiment of the matrix implant, high (about 40 to about 50%) superhydrolyzed PVA concentration polymeric matrices are provided. Small volumes (e.g., 3 ml or less) are advantageous when working with high concentrations of PVA to optimize the drug suspension in the matrix.

After these matrices are made into dried sheets, 1×1×2 mm rectangular pieces can be cut from the sheet, each representing a microimplant, for placement into animal eyes with smaller vitreous volumes (e.g. mouse, rat, or rabbit). Each microimplant has drug dispersed as in the single mode matrix implant described above. The advantage of high concentrations of superhydrolyzed PVA is there is negligible expansion of the implant if superhydrolyzed PVA (such as Airvol 125) is used. This lack of expansion is critical when placing these microimplants in small eyes since they are less likely to damage the lens and retina. These microimplants are useful for releasing drugs in the vitreous cavity to assess their efficacy in animal models of disease. These microimplants can also be employed as inlays that attach to reservoir implants, as described elsewhere herein. These inlays attached to the reservoir implants can be employed for animal models as well as in humans that require an intravitreal implant.

As mentioned above, where PVA concentrations higher than about 10 to about 15 wt % are used in making a matrix implant, such as about 50 wt % PVA, the sandwich glass plate technique is preferably used to help flatten out this highly viscous matrix. Subsequent cooling and removal of the top plate, enables the matrix to have uniform thickness upon drying.

In another embodiment, the matrix implant can be assembled with a suture stub to which the implant is attached. Suture stubs are used primarily for holding implants, whether of the matrix type or reservoir type described elsewhere herein, in the vitreous cavity or beneath the sclera. Thus, the stubs generally are not biodegradable.

The suture stub can be formed of a biocompatible, aqueous-insoluble polymer, such as crosslinked PVA. The suture stubs can be made, for example, using non-super hydrolyzed, high viscosity (62–72 cPs) polyvinyl alcohol (hydrolysis <99%) to increase bonding to hydrophobic surfaces. A suitable non-super hydrolyzed, high viscosity polyvinyl alcohol for use in making the suture stubs includes, for example, Airvol 350 obtainable from Air Products and Chemicals, Inc., Allentown, Pa., U.S.A. The polyvinyl alcohol is thermally crosslinked. The act of heating with or without radiation generally crosslinks the PVA sufficiently that the addition of a chemical crosslinker is not necessary. Optionally, a chemical crosslinker can be used while the PVA is dissolving in solution, i.e., before it is dried into a sheet, when a more rigid suture stub is required, for example, when larger implants need to be secured in the vitreous cavity. In this situation, the PVA is cured into the desired suture stub dimensions including previously added conventional chemical crosslinking agents for that purpose, and preferably those that are non-formaldehyde based crosslinking agent are used. These optional chemical crosslinkers include certain aldehydes such as glyoxal, glutaraldehyde, hydroxyadipaldehyde, and salts of multivalent anions such as zirconium ammonium carbonates. For the purpose of reducing the potential for ocular toxicity, a non-formaldehyde based crosslinking agent is preferred. Examples of suitable crosslinkers in this regard include Polycup 172 (1–4% d/d; Hercules, Inc.), which is a water soluble polyamide-epichlorohydrin-type resin, and Bacote-20 (2–10% d/d; Magneium Elektron, Ltd.), a zirconium ammonium carbonate salt. To prevent dissolution, the stubs are heated at about 130 to about 150° C. for about 5 to about 10 hours before use in the presence of a dispersed crosslinker. A silicone adhesive, such as MED1-4213 silicone adhesive (NuSil, Carpinteria, Calif.) can be used to bond the implants to the suture stub.

In another configuration, a portion of the outer surfaces of the implant, such as one side of the composite material matrix layer, has a polymer top coat that is impermeable to the therapeutic agent, such as polymethyl methacrylate (PMMA). PMMA, such as obtained from Sigma, can be prepared by dissolution of 1 g PMMA/10 ml acetone with stirring for about 12 hours. One side or a portion of the implant can be immersed in the resulting PMMA (e.g., three times over 30 minutes) and then dried (without heating). In this way, the release rate of the implant can be modified (viz., reduced), as desired.

As another alternative embodiment of the invention, poly(ethylene vinyl) acetate (EVA) is used in the polymeric matrix material in lieu of the superhydrolyzed PVA, all other things essentially the same in the construction. This provides an optional dual mode implant structure giving a loading dose followed by sustained slow release of drug. The EVA is non-bioerodible.

Figure 6:
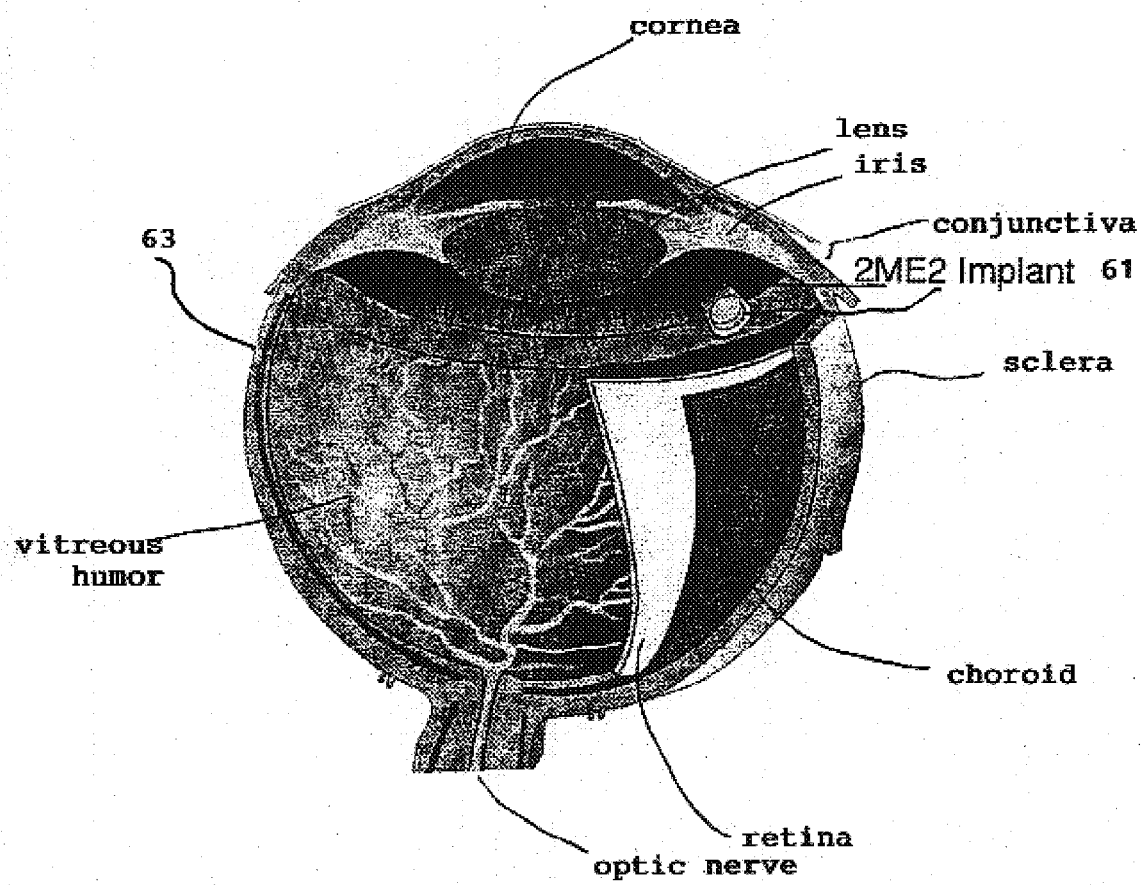
FIG. 6 schematically illustrates the placement in the eye of an intraocular matrix implant according to another embodiment of this invention.

These single mode and dual mode implant configurations are particularly well-suited for subconjunctival placement, but are not limited thereto and could be installed on or in other eye regions where convenient and useful, such as intravitreal placement using a suture stub. For instance, FIG. 6 is a schematic representation of a 2ME2-containing intraocular matrix implant 61 in an eye 63.

In administration, the subconjunctival matrix implant preferably is placed behind the surface epithelium within the subconjunctival space. This is done by a surgical procedure that can be performed in an out-patient setting. A lid speculum is placed and a conjunctival radial incision is made through the conjunctiva over the area where the implant is to be placed. Wescott scissors are used to dissect posterior to tenon's fascia and the implant is inserted. The conjunctiva is reapproximated using a running 10-0 vicryl suture. The eye has many barriers that do not permit easy penetration of drugs. These include the surface epithelium on the front of the eye and the blood/retinal barrier behind the eye that both have tight junctions. Thus, in one administration strategy of the invention, the dual mode or single mode matrix implant described herein is placed behind the surface epithelium in the subconjunctival space. These subconjunctival implants are generally about 1–2 mm in diameter for small rodent (i.e., mouse and rat) eyes, 3–4 mm in diameter for rabbit and human eyes and 6–8 mm in diameter for equine eyes.

Additionally, when the subconjunctival matrix implant is placed near the limbus (i.e., the area where the conjunctiva attaches anteriorly on the eye) to encourage the drug diffusion to enter the cornea, it is preferable to fixate the matrix implant with one or two absorbable sutures (e.g., 10-0 absorbable vicryl sutures). This is done by making holes with a 30 gauge needle in the peripheral portion of the implant, approximately 250–500 $\mu$m away from the peripheral edge of the implant. The holes are made 180 degrees from each other. This is done because subconjunctival matrix implants of this invention, when placed near the cornea, are at higher risk to extrude because of the action of the upper eye lid when blinking. When subconjunctival matrix implants of this invention are placed about 4 mm or more away from the limbus, the sutures are optional.

This matrix implant can deliver therapeutic levels of different pharmaceuticals agents to the eye to treat a variety of diseases. Using a rabbit model, drug released from the implant placed in the eye produces negligible levels of the drug in the blood. This significantly reduces the chances of systemic drug side-effects.

In either case, whether the dual mode or single mode variants, this embodiment of implant of this invention is well-tolerated and non-toxic to the patient or recipient, viz., a mammalian host-human or veterinary. In addition, this implant design of this invention is prepared by unique methodologies and selections of materials leading to and imparting the unique pharmacological performance properties present in the finished devices.

Among other eye therapies, the subconjunctival matrix implants of the present invention provide an effective treatment for corneal transplantation procedures, where it is desirable to delivery an immune system modulator agent such as cyclosporine A non-systemically to the eye, in order to reduce rejection rates of corneal allografts. The matrix implants containing 2ME2 can be attached to suture stubs and placed in the vitreous humor for used in treatment of CNVM. 2ME2 is a drug manufactured by EntreMed, Inc., Rockville, Md., U.S.A., and is currently referred to as "Panzem". The matrix implant also has potential for replacing the need for topical eye drops to treat certain eye diseases like glaucoma and uveitis and the implant has the potential to treat eye diseases in the back of the eye that are potentially sight-threatening (e.g., retinal disease).

Also, for either the matrix implant, or the reservoir implant described infra, the drug released for the loading dose can be different than the drug that is released for the long-term maintenance dose. For example, it may be advantageous to have a loading dose of corticosteroid from the dual mode implant for about a month postoperatively to reduce the inflammatory response resulting from surgery and have a continuous release of different drug to effect the disease that is being treated.

The drug pellets or tablets used for either the dual mode matrix implants, or the intraocular reservoir implants described elsewhere herein, are made by compressing a free-flowing powdered form of the drug in any suitable compression or molding machine, such as a pellet press. Pellet presses can be obtained, for example, from Parr Instrument Company, Moline, Ill. A force transducer can be used in ways one skilled in the art will appreciate to closely manage the compressive force applied. In the pellet press, the powdered form of the drug is enclosed within an open-mouthed cylindrical receptacle having a solid base and a continuous inner wall defining the radial diameter and length (thickness) of the pellet to be formed. A ram applies a controlled uniform amount of pressure across the exposed surface of the powder for a given period of time sufficient to consolidate the powder into a free-standing solid pellet form.

Depending on the drug, binders and excipients for pellet-making optionally can be used. For example, magnesium stearate or hydroxypropylmethyl cellulose could be used. For example, for CsA pellets (using 0.04% magnesium stearate as a binder) to be used in corneal transplantation treatments, a compressive pressure of about 110 lb-force is used (for a round pellet, 3 mm diameter, 2 mm length) For 2ME2 pellets for use in treatment of CNVM, a micronized preparation of 2ME2 (size of drug particle is <5 micrometers) is used without binders, and a pressure of about 190 lb-force is used (for a round pellet, 2 mm diameter, 3 mm length). The pressure consolidates the powder into an integral, discrete solid pellet or tablet.

Reservoir Implants:

FIGS. 8A–I and 10A–D show methods for fabricating intraocular reservoir implants according to this invention. The reservoir implants are sustained-release devices which deliver therapeutic agent to the eye over a prolonged period of time. With some modifications described herein, a loading dose or dual mode release capability also can be added to the reservoir implants.

The reservoir implants generally include an implant reservoir subassembly, a suture stub or other attachment means, and a means to adhere those two features together.

In general, the suture stub attachment means and adhering means include the same respective materials described supra in connection with suture stubs optionally usable with intravitreal matrix implants, and reference is made thereto.

As an alternative to the suture stub, a silk mesh fabric can be embedded in one end of the reservoir type implant. This allows a suture to pass through the one end and the suture will not scissor through the soft silicone since it is caught by the mesh. The suture then passes through the edges of the scleral wound and is tied down.

The discussion turns now to a method of making reservoir implant subassemblies according to an embodiment of the reservoir implants of the invention.

Figure 8A:
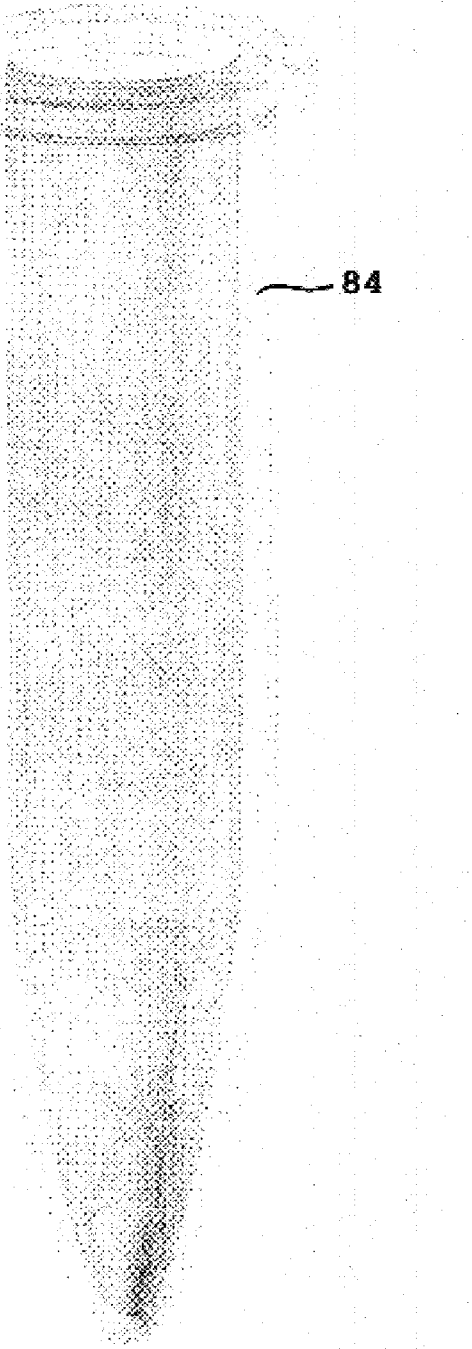

Referring to FIG. 8A, a microcentrifuge tube 84 is provided of plastic construction, such as polyurethane, polypropylene or high density polyethylene construction, of suitable dimensions (e.g., ID of about 10 mm and a length of about 40 mm), which can be obtained from Peninsula Laboratories Inc., Belmont, Calif. As shown in FIG. 8A, the microcentrifuge tubes have a tapered, conical-shaped bottom and cylindrical upper portion having an open end.

Figure 8B:
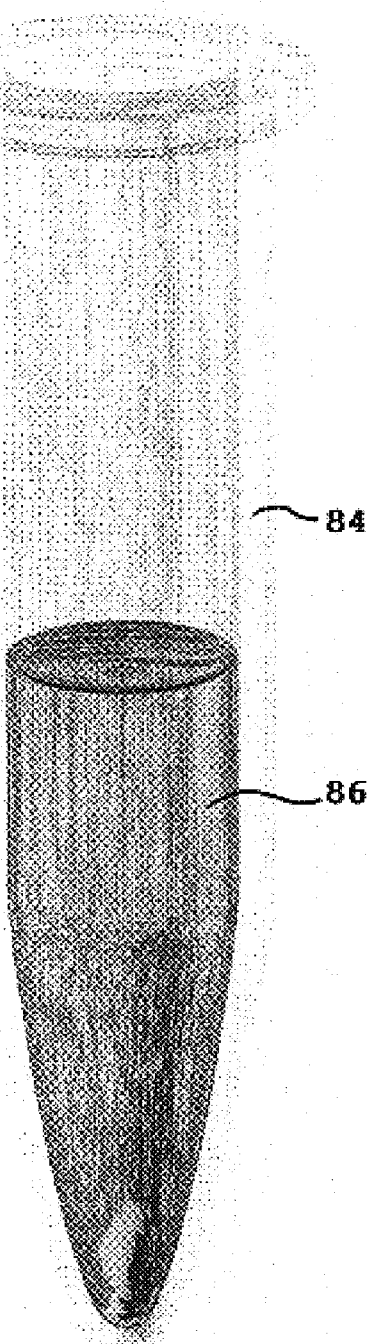

As seen in FIG. 8B, a curable (wet) silicone 86 fluid is poured into the lower section of the microcentrifuge tube 84 (e.g., about 10 mm depth).

The silicone used in making the reservoir implants is a medical grade silicone, and generally is a polydimethylsiloxane (PDMS)-based compound. The silicone used is biologically (physiologically) inert and is well tolerated by body tissues. Suitable silicones for use in the practice of this embodiment include "MED-6810" silicone, MED1-4213, MED2-4213 silicone, which can be obtained from NuSil, Carpinteria, Calif. Both of these silicones are two-part silicones including a metal curing system (e.g., Pt). The time and temperature needed to cure the silicone will depend on the silicone used and the drug release profile desired. These silicones, if left to cure at room temperature (e.g., 20–30° C.,) will require about 24 hours or more to cure. The cure rate will increase with increasing cure temperatures. For instance, MED2-4213 silicone will cure in about 30 minutes at about 100° C. As will be discussed in more detail below, the more quickly the silicone is cured, the less opportunity for therapeutic agent to leach out into the surrounding silicone. Thus, the more rapid the curing, the less likely any burst or loading dose will be yielded by the device along with the slow steady state release action.

Figure 8C:
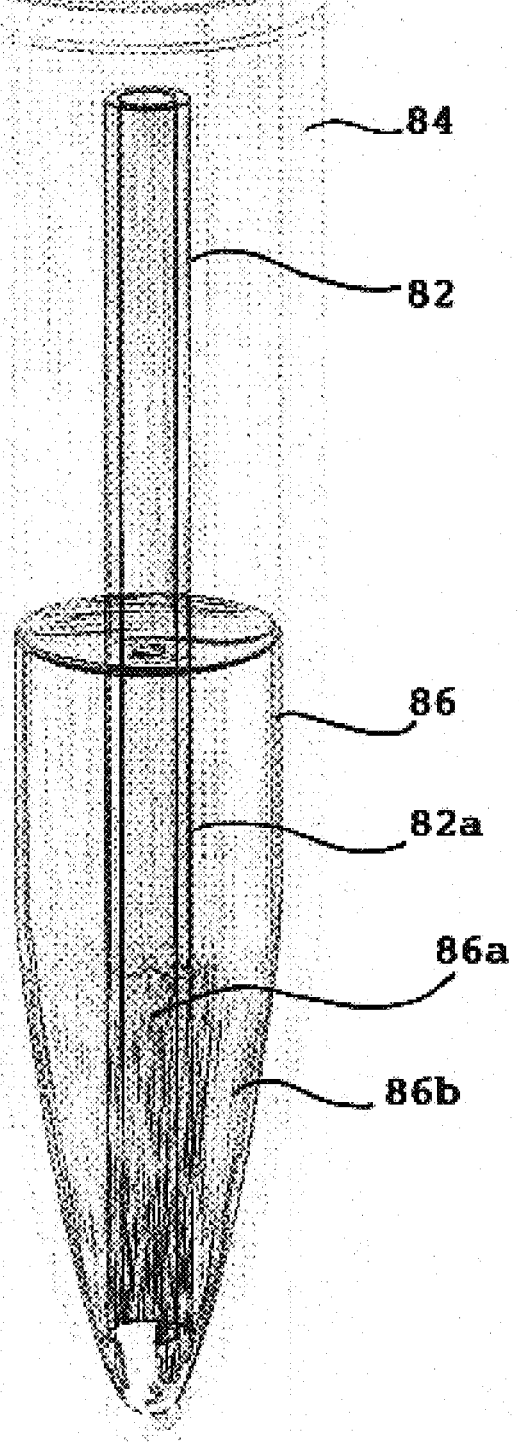

Referring to FIG. 8C, to provide a low adhesion, thin walled plastic tube 82 shown, thin walled coiled polytetrafluoroethylene tubing, viz., Teflon® tubing or the like releasable plastics, is heated at about 110° C. for about 30 seconds and then straightened, and thereafter cooled and set in the straightened orientation. The straightened low adhesion plastic was then cut into about 1.0 inch (2.54 cm) long tubes. The Teflon® tubing is selected so as to have an outer diameter less than the inner diameter of the microcentrifuge tube, and the inner diameter of this low adhesion plastic tube must be larger than the radial diameter of a pellet to be encapsulated therein with silicone, as discussed below.

Referring still to FIG. 8C, soon after the wet silicone is introduced into the microcentrifuge tube 84, one of the cut low adhesion plastic tubes 82 is placed within the microcentrifuge tube. The low adhesion plastic tube 82 is spun vertically down a distance within the centrifuge tube such that the lower end of the plastic tube 82 is submerged a distance "d" (e.g., about 3 mm) below the surface of the silicone 86 already in the microcentrifuge tube 84 (distance "d" is best seen in FIG. 8E). The centrifuge device used can be a TOMY MTX-150 centrifuge, obtained from Peninsula Laboratories Inc., Belmont, Calif. The submerged portion 82a of the plastic tube 82 is indicated in FIG. 8C. A portion 86a of the silicone 86 fills the lower 3 mm of the plastic tube 82, but another portion 86b fills space between the outside surface of the tube 82 and the inner wall of the tube 84 in the lower section of the tube 84.

Soon after introducing the tube 82 into microcentrifuge tube 84 in this manner, the microcentrifuge tube 84 is centrifuged to degas the wet silicone 86 and to radially center the tube 82 inside the outer tube 84.

At this juncture, the microcentrifuge tubes and contents are held at room temperature (or optionally higher temperatures) until the silicone 86 cures and solidifies, generally about 24–72 hours for room temperature cure. This hardens the portion of silicone 86a located inside the lower end of the plastic tube 82, providing a solid silicone base 86a inside tube 82, and a hardened silicone 86b outside tube 82 which serves to retain it in an upright position.

Then, and as shown in FIG. 8D, a drug pellet 88 is introduced into the plastic tube 82 followed by adding additional uncured silicone fluid 86c into the tube 82. The microcentrifuge tube 84 is then centrifuged as needed to degas the additional silicone 86c and place, if necessary, the pellet 88 on the silicone base 86a positioned at the bottom portion 82a of the plastic tube 82. The additional uncured silicone 86c added inside the plastic tube is sufficient to completely immerse the exposed surfaces of the pellet 88 as it rests on the pre-hardened silicone base 86a. As needed, the drug pellet 88 can be manually or mechanically centered on the silicone base 86a before curing silicone 86c using an insertable/retractable device or probe (such as a triple-0 Bowman probe) to move and center the pellet 88. The added silicone fluid 86c is then cured inside the top portion 82b of the plastic tube 82.

Figure 8H:
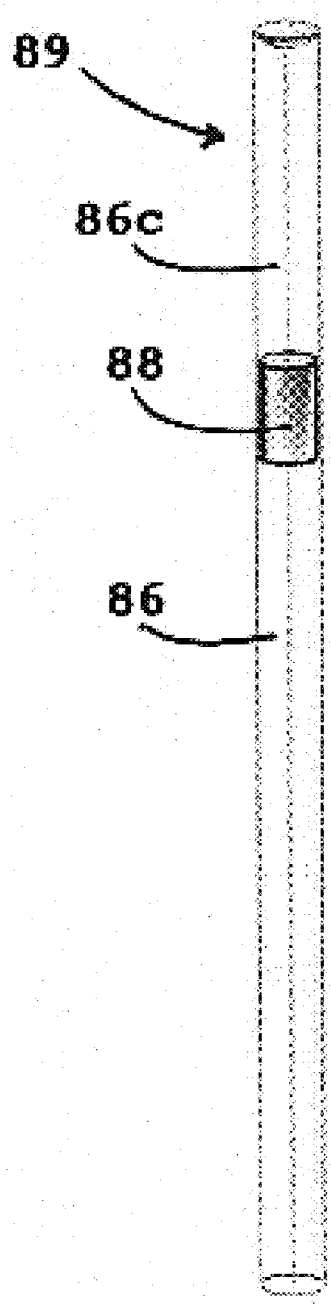
Figure 8I:
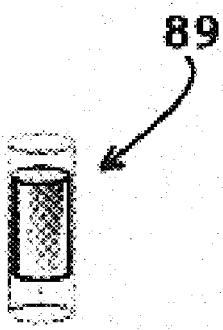
Figure 9A:
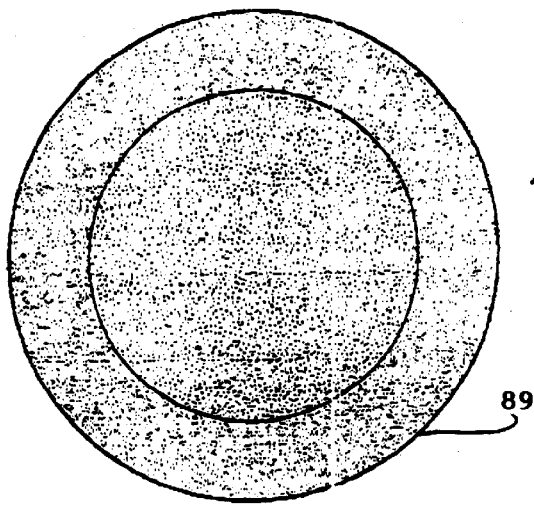
FIGS. 9A–C depicts top, perspective, and front views, respectively, of a reservoir implant (subassembly) according to a reservoir type implant of this invention.
Figure 9B:
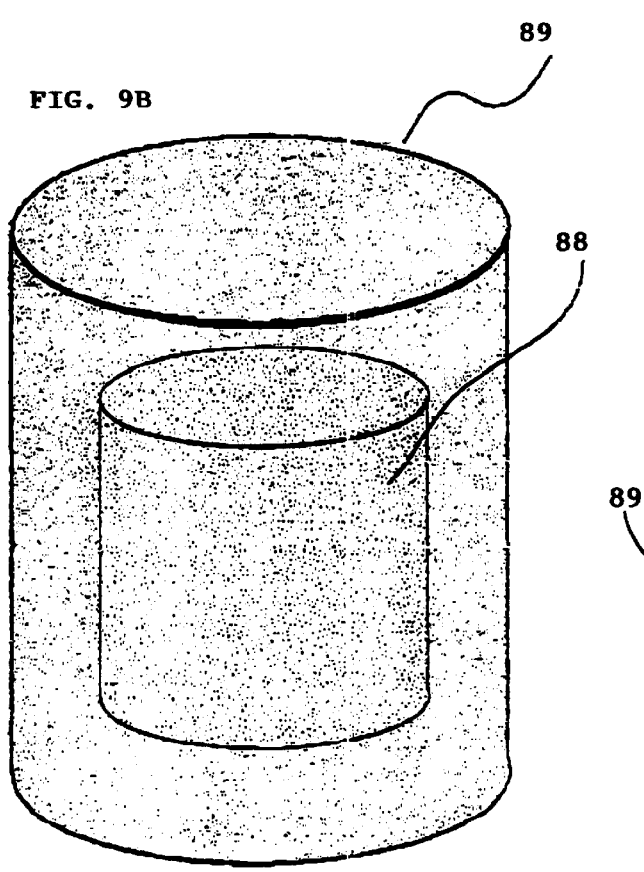
Figure 9C:
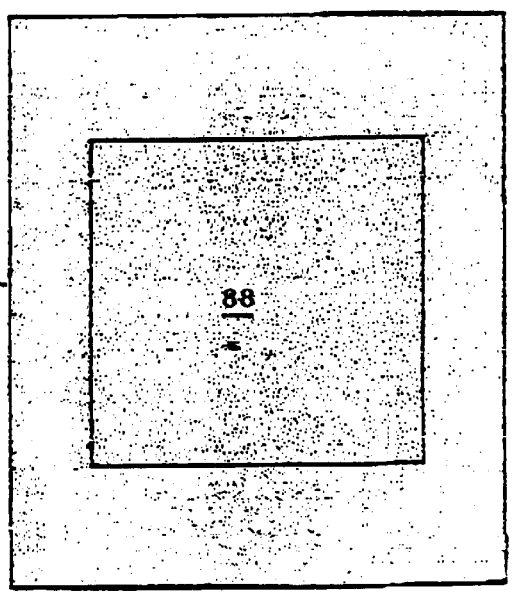

As shown in FIG. 8E, the microcentrifuge tube 84 is then removed by sharp dissection thereof with care taken not to disrupt the plastic tube 82 or its contents. All of the silicone portions 86a, 86b and 86c remain with the tube 82 at this juncture. Then as illustrated in FIG. 8F, the silicone portion 86b is manually separated from the exterior of tube 82 leaving tube 82 containing silicone portion 86a and 86c sandwiched over the pellet 88. Next, as shown in FIG. 8G, plastic tube 82 is removed by sharp dissection in which the plastic tube 82 has a transverse cut made at the lower end thereof with a blade, and the tube 82 is then split away from the internal silicone/pellet complex subassembly 89. FIG. 8H shows the internal silicone/pellet complex subassembly 89 after removal of the low adhesion plastic tube 82. As shown in FIG. 8I, the top and bottom ends of the reservoir implant subassembly are trimmed closer to the top and bottom ends of the drug pellet 88 to provide a finished reservoir implant subassembly 89. FIGS. 9A–C show various enlarged views of the resulting reservoir implant subassembly 89 comprised of the silicone-encased drug pellet.

Figure 7:
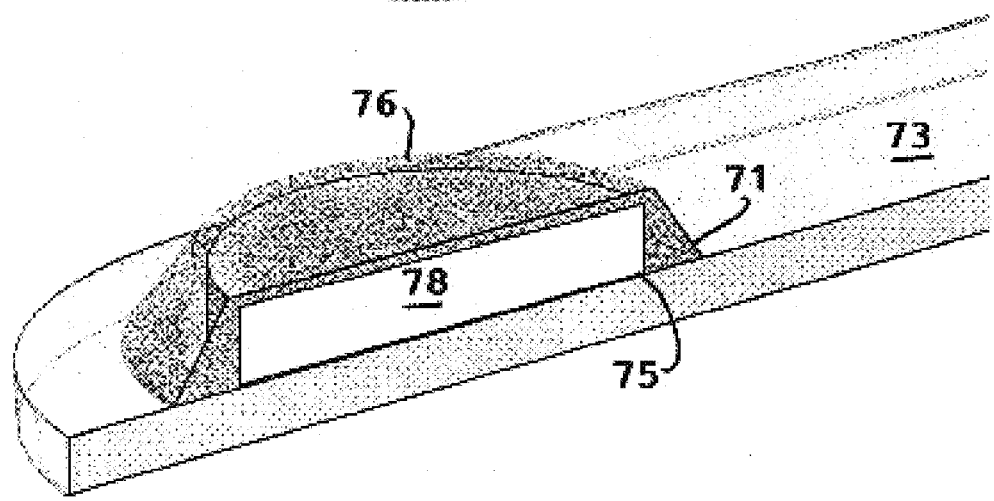
FIG. 7 is enlarged view, in cross-section, of a sustained release intraocular implant device according to another embodiment of the invention a drug pellet surrounded by a permeable polymeric material including optional additional drug, and an eye attachment means.

Referring now to FIG. 7, a reservoir implant subassembly 71 made in this manner is attached to a suture stub 73, such as one constructed of processed Airvol 650 as described above, using a silicone adhesive 75, such as Nusil MED1-4213. The suture stub can be used to fasten the implant reservoir in the eye such that it cannot drift or move about.

Figure 12A:
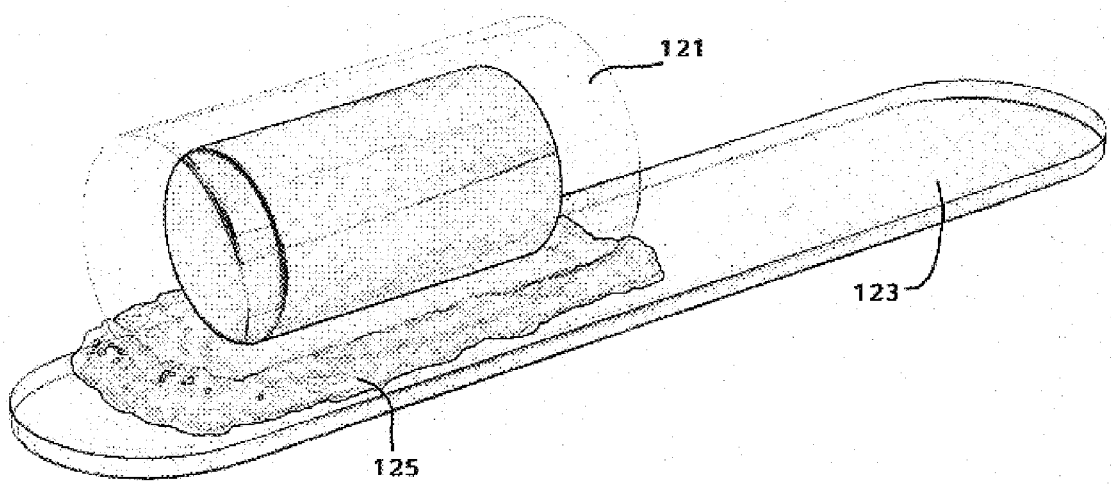
FIG. 12A schematically illustrates an intravitreal reservoir single mode implant according to an embodiment of the invention.
Figure 13:
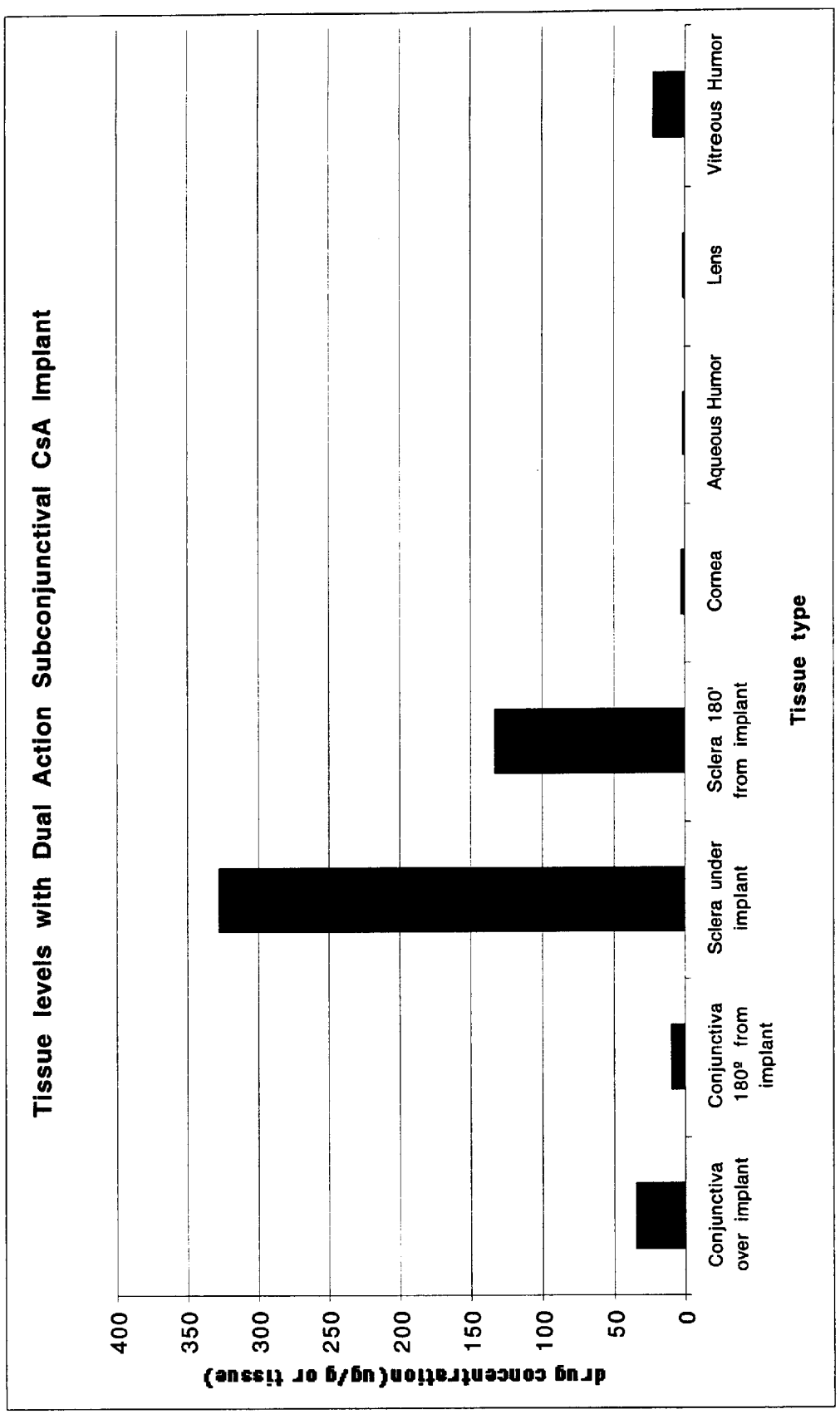
FIG. 13 graphically shows ocular tissue levels of a drug (CsA) at different locations as delivered by a dual mode matrix implant of this invention implanted in the subconjunctival space, as described in Example 4.
Figure 14:
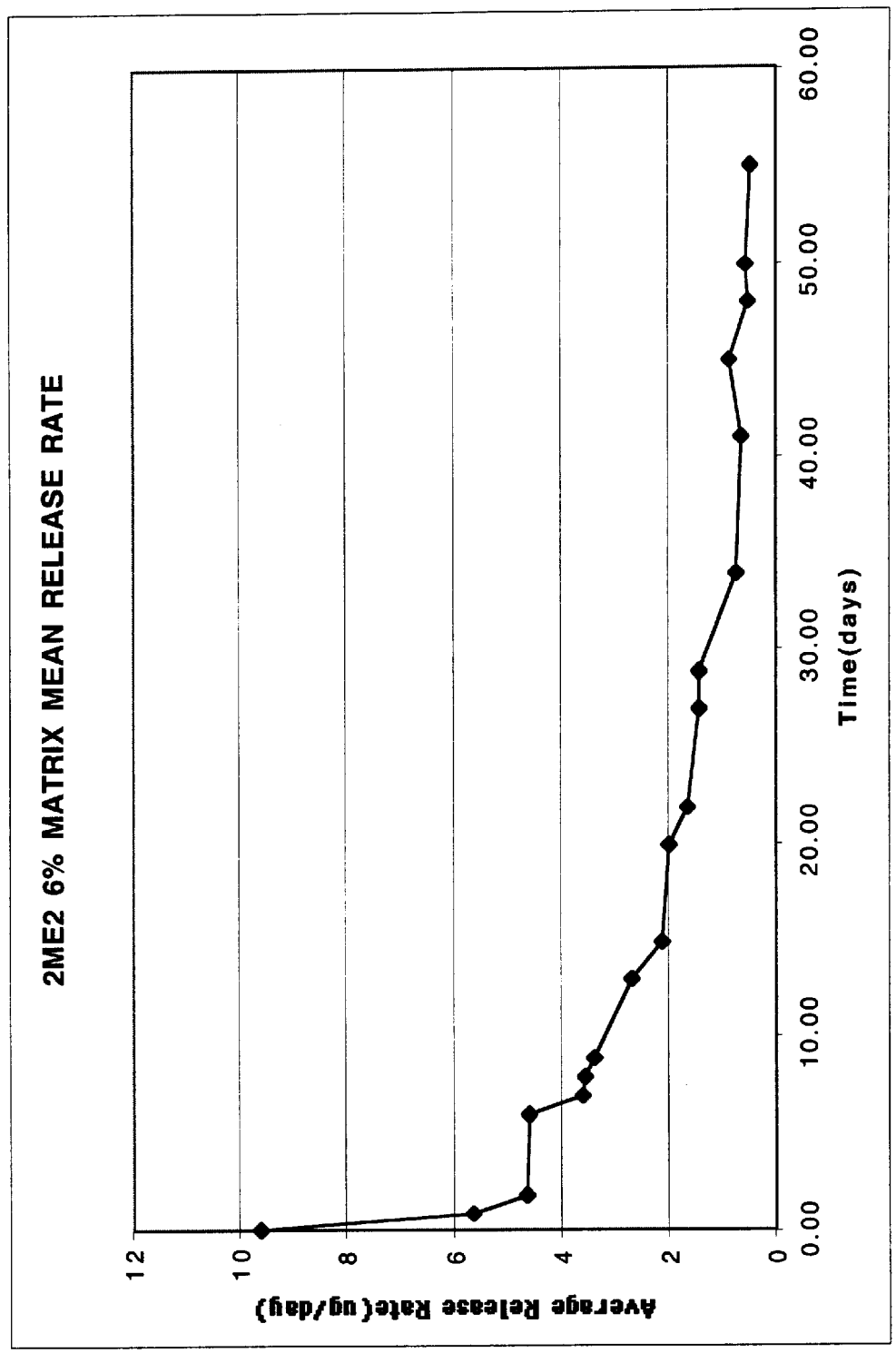
FIG. 14 graphically shows the average in vitro release rate of a drug (2ME2) over time as delivered by a matrix implant of this invention suitable for placement in the vitreous, as described in Example 5.

Reservoir implant subassemblies 121 made in this manner with various drugs in the reservoir, e.g., leflunomide (lef) or 2-methoxyestradiol (2ME2), have been adhered to Airvol 350 suture stubs using silicon adhesive (see FIG. 12A) in order to examine the release properties. For each drug, 3 different diameters (inner) of Teflon® tubing were used to make implants with polymer thicknesses (i.e., 0.20, 0.36, and 0.70 mm), as described in Example 8 infra, to provide a thin-walled "mold" for the radial dimensions of the silicone encasement to be formed around the pellet. As seen in FIGS. 13 and 14, the reservoir implants had lower release rates with increasing polymer thickness, radial and/or top/bottom, surrounding the drug pellet.

By varying the sizes of pellets and Teflon® tubing it is possible to create many thicknesses of polymer surrounding the implant, as shown in Table A below. Table A reports such polymer thicknesses for various pellet sizes and various tube gauges (i.e., 8, 9, and 10 gauge). A typical releasable tubing used is PTFE (Texloc, LTD. Fort Worth, Tex.). The release rate of a reservoir implant according to this invention is strongly dependent upon the thickness of the polymer coating. For a cylindrical reservoir implant device containing a cylindrical drug pellet radially centered within the silicone cladding, this relationship is described by the following formula:

$$dM_t/dt = 2\pi h DKC_s/(\ln r_0/r_1)$$

where $dM_t/d_t$ is the release rate, $r_0$ is the outside radius of the implant, $r_1$ is the radius of the drug pellet, h is the height of the cylinder, D is the diffusion coefficient of the drug through the polymer, K is the distribution coefficient and $C_s$ is the solubility of the drug in the fluid.

TABLE A

| Pellet Diam. | Thickness of Polymer Coating (mm) Tubing Sizes (gauge) | | |
|---|---|---|---|
| (mm) | 8 | 9 | 10 |
| 0.5 | 1.45 | 1.26 | 1.11 |
| 1.0 | 1.20 | 1.01 | 0.86 |
| 1.5 | 0.95 | 0.76 | 0.61 |
| 2.0 | 0.70 | 0.51 | 0.36 |
| 2.5 | 0.45 | 0.26 | 0.11 |
| 3.0 | 0.20 | 0.01 | 0 |

This method for preparing the intraocular reservoir implant of this invention provides an implant having a controlled radial thickness of degassed silicone cladding around the drug pellet with no significant variability in the cladding thickness from one coated pellet to the next. Also, rigorous post-production quality control inspections (including measuring individual implant release rates before in vivo use) of the implant products are not necessary, which reduces the chances for contamination of the device from additional handling as well as the cost of making the devices. Drug pellets of the medicament can be made using a Parr pellet press, as described earlier.

Figure 12B:
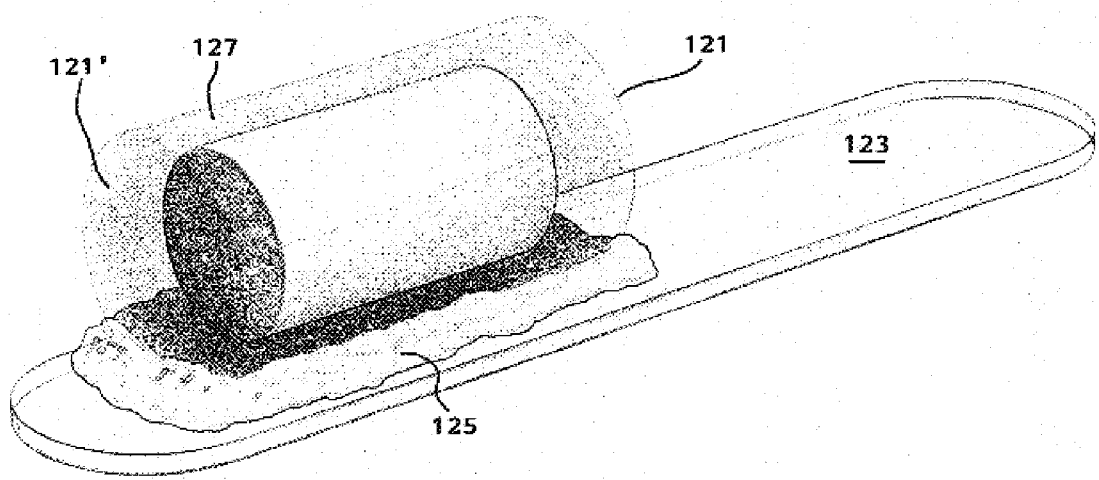
FIG. 12B schematically illustrates a dual mode intravitreal reservoir implant according to an embodiment of the invention, including therapeutic agent in the silicone surrounding the drug pellet.
Figure 12C:
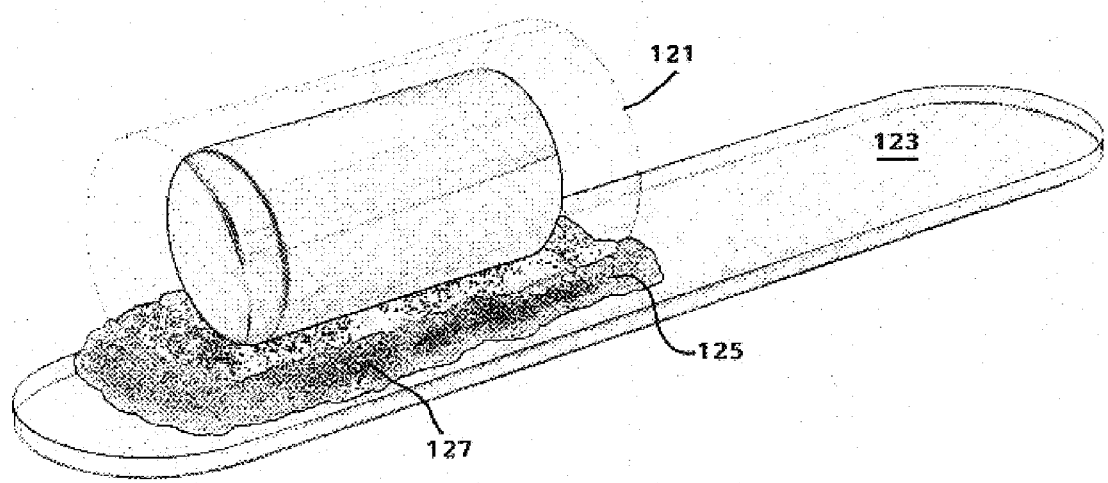
FIG. 12C schematically illustrates an intravitreal reservoir dual mode implant according to an embodiment of the invention, including therapeutic agent in a silicone adhesive used to attach the reservoir implant subassembly to the suture stub.
Figure 12D:
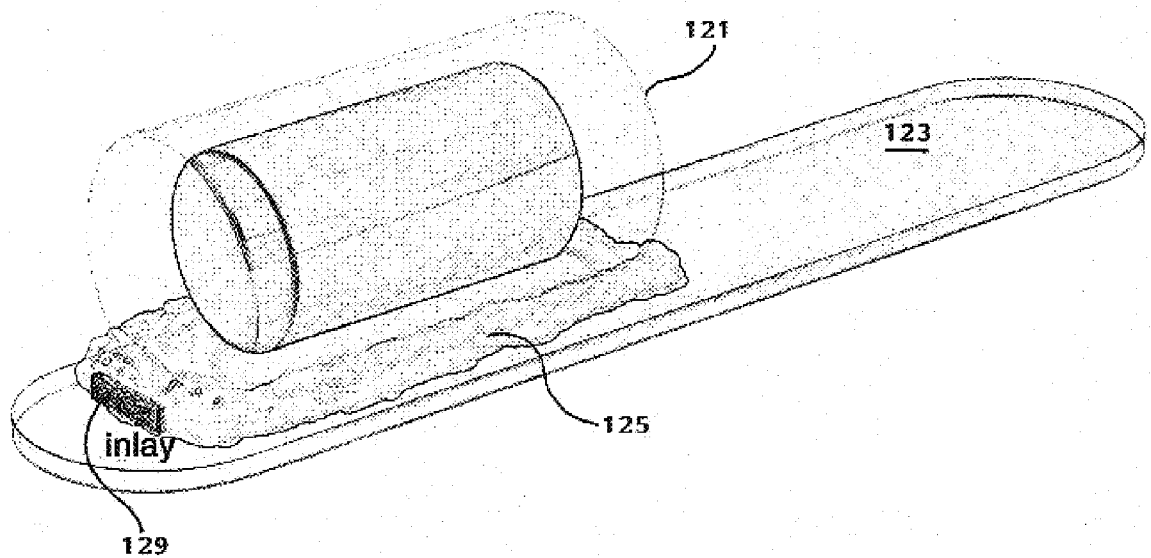
FIG. 12D schematically illustrates an intravitreal reservoir dual mode implant according to an embodiment of the invention, including therapeutic agent in an inlay attached to a silicone adhesive used to attach the reservoir implant subassembly to the suture stub.
Figure 12E:
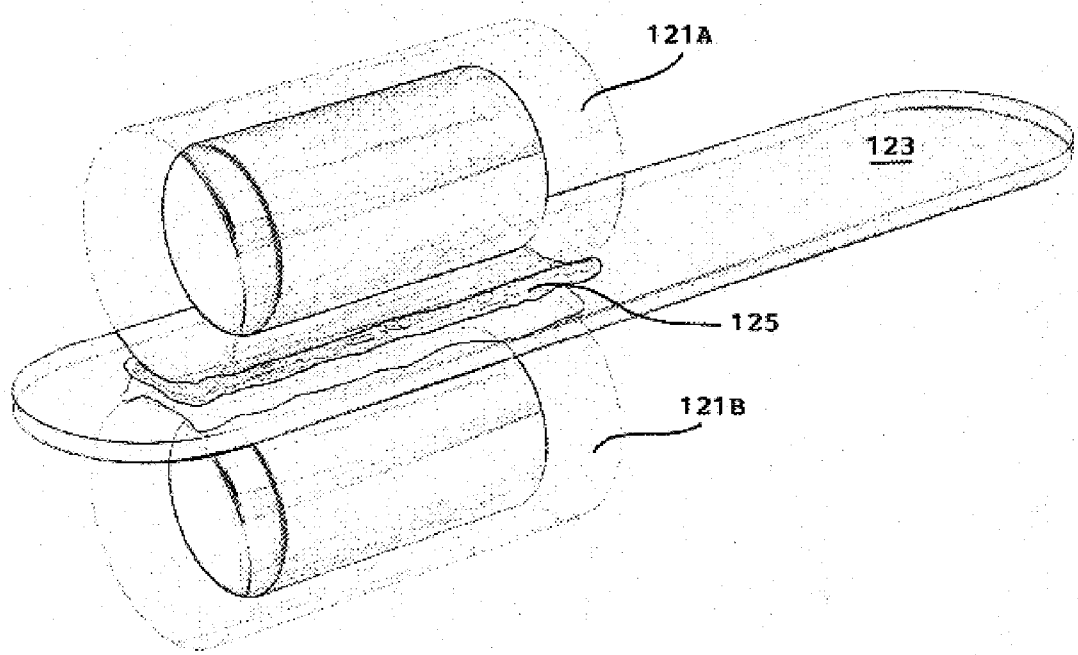
FIG. 12E schematically illustrates a double-barreled intravitreal reservoir implant configuration according to an embodiment of the invention.

Modifications available to adjust the drug administration of the reservoir implants include:

an intravitreal reservoir dual mode implant further including therapeutic agent 127 dispersed in the silicone 121' surrounding the drug pellet 121" of the reservoir implant subassembly 121 (FIG. 12B);

an intravitreal reservoir dual mode implant including therapeutic agent 127 dispersed in a silicone adhesive 125 used to attach the reservoir implant subassembly 121 to the suture stub 123 (FIG. 12C);

an intravitreal reservoir dual mode implant including therapeutic agent provided in an inlay 129 attached to a silicone adhesive 125 used to attach the reservoir implant subassembly 121 to the suture stub 123 (FIG. 12D); and a double-barreled intravitreal reservoir implant configuration including two reservoir implant subassemblies 121A and 121B attached to a common suture stub 123 (FIG. 12E). This configuration effectively increases the surface area of drug release from the central pellet to correspondingly increase the maintenance release rates.

Figure 11C:
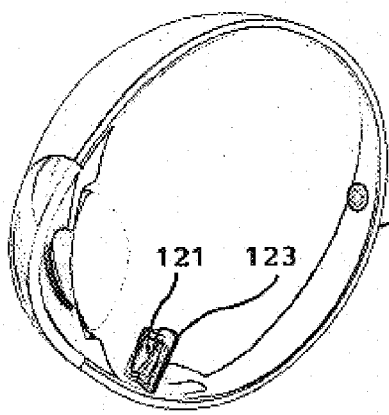
FIG. 11A schematically illustrates the delivery of a loading dose by an intravitreal reservoir dual-mode implant of this invention, which has been placed in an eye as shown in FIG. 11C.
FIG. 11B schematically illustrates delivery of a maintenance dosage by the intravitreal reservoir dual mode implant shown in FIG. 11A, subsequent to delivery of the loading dose.
Figure 11A:
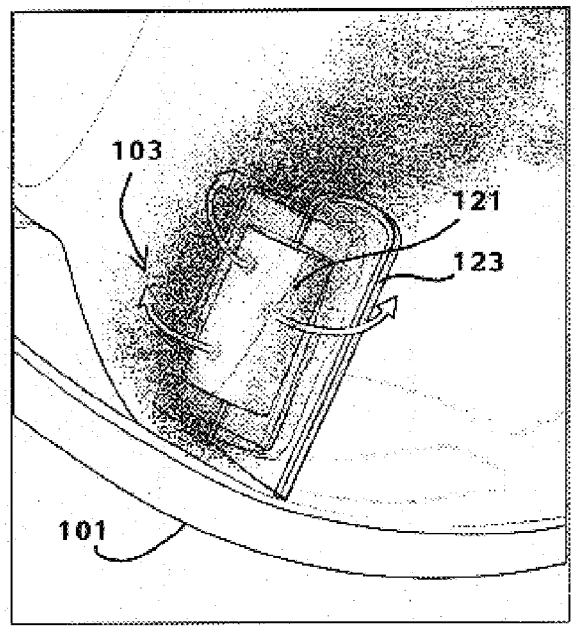
Figure 11B:
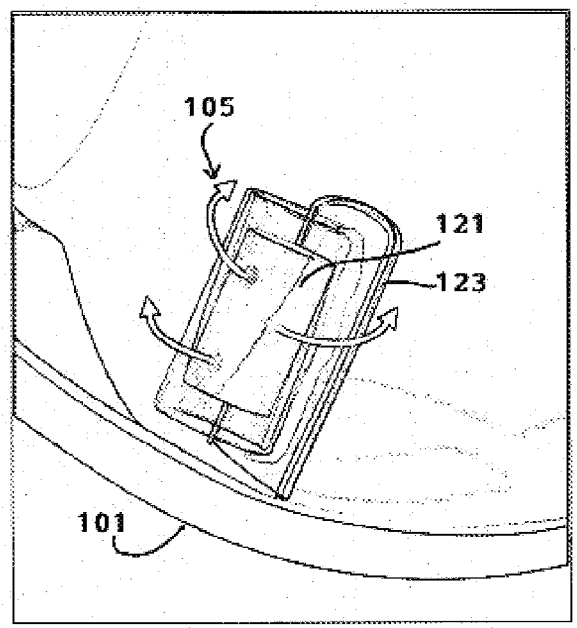

The drug delivery behavior of the intraocular reservoir implants (121, 123), as mounted on a suture stub as described above, is schematically shown in FIGS. 11A (initial loading dose 103) and 11B (long term sustained or maintenance dose 105), for an implant placed in an eye 101 as shown in FIG. 11C.

Figure 10A:
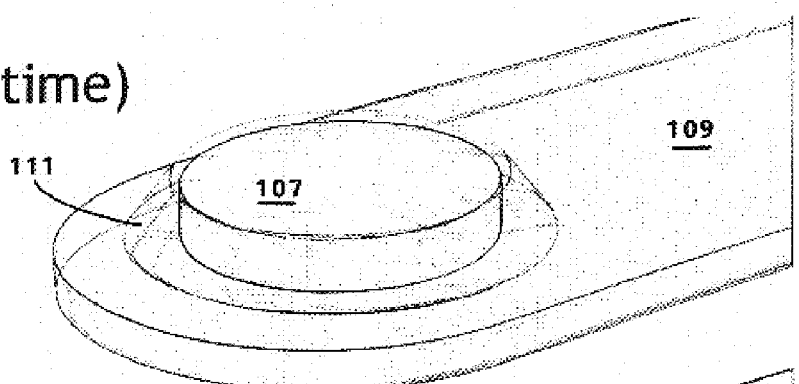
FIGS. 10A–D schematically depict an enlarged view of diffusion of therapeutic agent into an uncured silicone bead surrounding a drug pellet at different time intervals (0 min., 30 min., 2 hr., and 24 hr., respectively) in a step associated with the making of a reservoir implant according to a "delay in cure" technique of yet another embodiment of this invention.
Figure 10B:
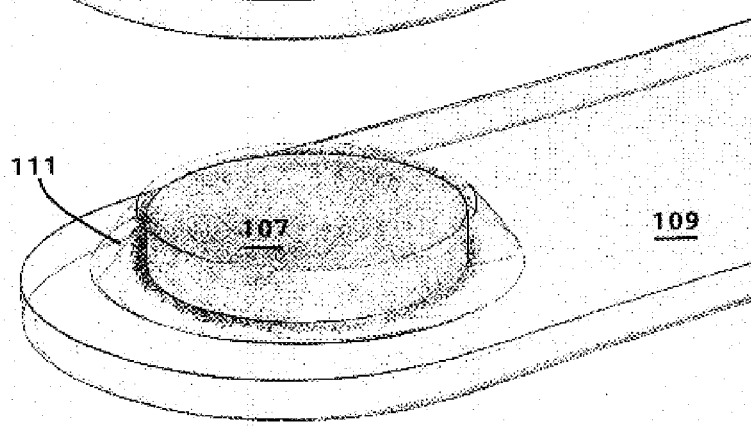
Figure 10C:
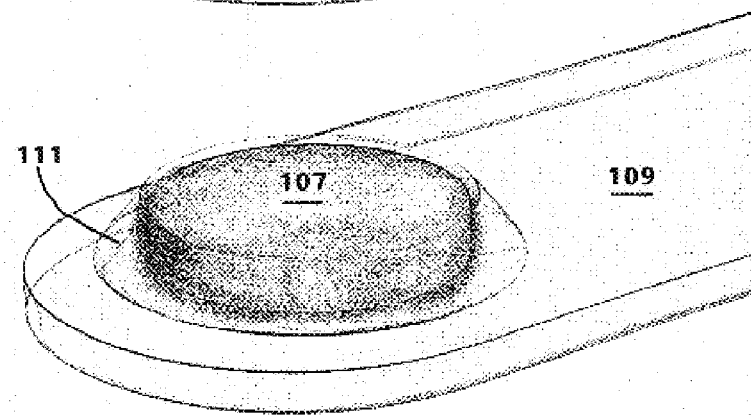
Figure 10D:
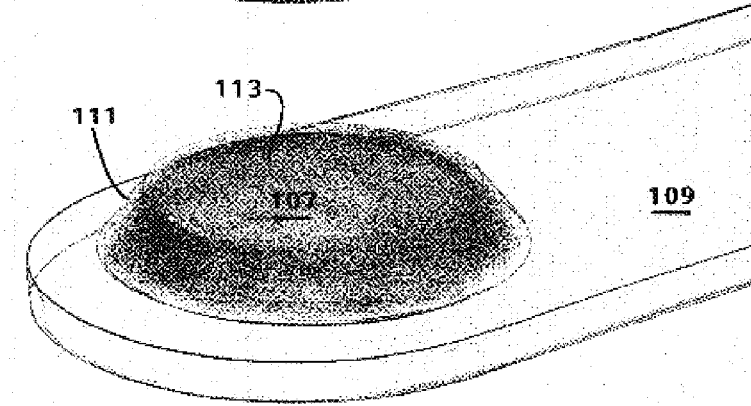
Figure 10E:
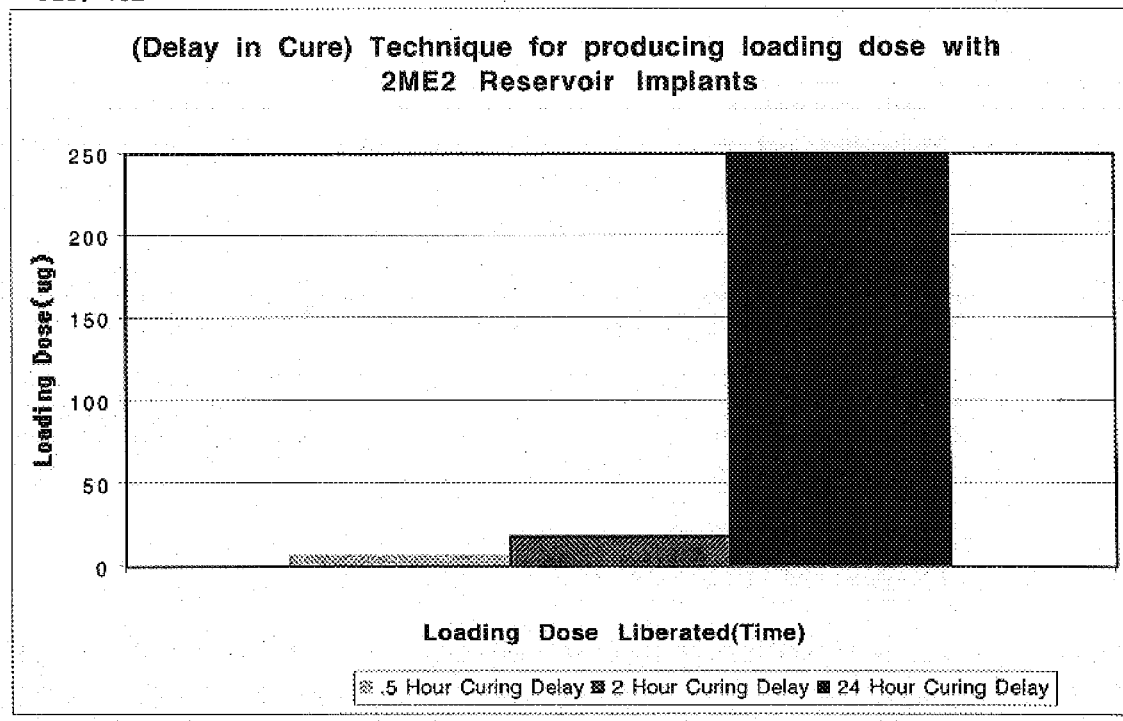
FIG. 10E is a graphical illustration of in vitro loading doses in PBS achieved with 2ME2 reservoir implants of the type described in connection with FIGS. 10A–H herein, as a function of the delay in cure time.

As another dual mode embodiment of the reservoir implant, and as shown in FIGS. 10A–D, a circular wafer shaped pellet 107 of therapeutic agent, which has a tablet shape by having a larger radial diameter than thickness, is fixed at its lower surface to a suture stub 109 with silicone adhesive (not shown), such as the above-mentioned Nusil MED1-4213 silicone adhesive. The dimensions of the wafer-shaped pellet or tablet could be, for example, 1–2 mm in height and 3 mm in radial diameter. A temperature-curable silicone adhesive, such as the same type above (e.g., NuSil MED1-4213 silicone adhesive), is then used to form a bead or ribbon of wet silicone 111 around the periphery of the tablet 107 (i.e., coating the side edge surfaces of the tablet and contacting the adjoining surface of the suture stub). Then, the cure of the silicone bead coating is slowed or delayed preferably for about 18 to 30 hours, more preferably approximately 24 hours, by keeping the coated assembly at room temperature (e.g., 20–30° C.). The upper flat surface of the tablet is covered with thin silicone coating 113, such as MED1-4123 or Nusil MED-6810 (a two-part silicone) that is cured with (radiant) heat before or after the "delay in cure" procedure is conducted on the peripheral silicone bead coating. During the interim delay in cure period when the silicone adhesive is gradually and slowly curing, some, but not all, of the therapeutic agent diffuses into the surrounding unfully cured bead of silicone polymer, which creates a significant burst or loading dose when the implant is installed, followed by slow, lower dosage sustained release of the therapeutic agent. This effect is shown by FIG. 10E, which relates to in vitro tests performed on this class of reservoir implants where the tested implants included 2ME2 tablets of about 1.5 mm height and 3 mm in diameter, the bottom and peripheral bead silicone adhesive was NuSil MED1-4213 silicone adhesive, and the top surface silicone coating was Nusil MED-6810 applied and cured after the "delay in cure" procedure.

Certain silicones, such as MED1-4123, that contact the drug pellet in a wet phase for a long period of time, yield more substantial loading dosages. By using this drug leaching to advantage, and using silicones that can quick cure (MED2-4123 or the 6810), it is possible to control the degree of drug loading by curing at differential times.

The reservoir implants of this invention can be used to treat a number of eye diseases and indications including, for example, age-related macular degeneration, glaucoma, diabetic retinopathy, uveitis, retinopathy of prematurity in newborns, choroidal melanoma, chorodial metastasis, and retinal capillary hemangioma. For these indications, a suitable therapeutic agent includes, for example, 2-methoxyestradiol. For example, the reservoir implant provides for a sustained release of drugs, such as 2-methoxyestradiol for the treatment of undesirable angiogenesis involved in the degeneration of the macula.

The loading dose from the reservoir implant can be estimated when the target drug concentrations in the vitreous and drug clearance from the eye is known. Assuming a one-compartment model with no partitioning, the steady-state concentration (Css) is the release rate times bioavailability (F) divided by the clearance (CL). Benet, L., et al., Pharmokinetics In: Goodman and Gilman's: The Pharmacological Basis of Therapeutics. New York: McGraw-Hill; 1996: 3–27. This relationship is expressed by the following formula:

$$(Css) = \text{steady-state implant release rate} \times F/CL \quad (1).$$

The fractional bioavailability of the dose (F) can be assumed to be 1 for intravitreal implants and <1 for subconjunctival implants (since some drug is lost en route to the vitreous cavity through the conjunctival, episcleral, and choroidal vasculature). Classic pharmacokinetics teach that steady state concentrations can be obtained after approximately four half-times. For example, the CL of an antimetabolite from the vitreous cavity, when scaled to humans, is 0.38 ml/hr and the half life is 10.4 hours. Velez, G., et al., Intravitreal Chemotherapy for Primary Intraocular Lymphoma. *Arch Ophthalmol* (*in press*). 2001.

If the target concentration in the vitreous is 1 μg/ml, a release rate of 0.38 μg/hr will be required to achieve Css in the vitreous after approximately 4 half times or 41.6 hours. For comparison, if the drug is being released by a subconjunctival matrix implant according to this invention, with a bioavailability of 0.5, the release rate from the implant would need to be doubled (i.e., 0.76 μg/hr).

For conditions, such as CNVM associated with AMD, long delays (i.e., 41.6 hours) are not desirable. Loading doses from the implant can shorten the length of time required to reach Css. For example, using the equation:

$$V_d^*(dC/dt) = I(t) - CL^*C(t)$$

where $V_d$ is the volume of distribution, C is the concentration of distribution, dC/dt is the rate of change of concentration in the vitreous, I(t) is the release rate from the implant. The notation with parentheses (t) indicates that the rate may change with time, for example, a rapid release on and then settling to a lower rate for a prolonged period of time.

A doubling of the release rate of an intravitreal implant for a period equal to the half-life of the drug allows Css to be reached in one half-time (10.4 hours) instead of four half-lives (41.6 hr). To further increase the speed at which the Css is reached, for example, in 2 hrs (20% of a half-life) after the implant is placed, the drug release rate should be approximately 8 times higher during that period.

The reservoir implants have been designed to release a loading dose of drug within the first few hours after implant placement. For example, using the 'cure time delay' technique, periods of delay in the curing the silicone around the drug pellet can change the drug burst from the implant; however, the reservoir implants continue to release a steady state concentration after the loading dose.

The therapeutic agents and drugs that can be delivered by the various matrix and reservoir implants of this invention include, for example:

antibiotic agents such as fumagillin analogs, minocycline, fluoroquinolone, cephalosporin antibiotics, herbimycon A, tetracycline, chlortetracycline, bacitracin, neomycin, polymyxin, gramicidin, oxytetracycline, chloramphenicol, gentamicin and erythromycin;

antibacterial agents such as sulfonamides, sulfacetamide, sulfamethizole, sulfoxazole, nitrofurazone, and sodium propionate;

antiviral agents such as idoxuridine, famvir, trisodium phosphonoformate, trifluorothymidine, acyclovir, ganciclovir, DDI and AZT, protease and integrase inhibitors;

anti-glaucoma agents such as beta blockers (timolol, betaxolol, atenolol), prostaglandin analogues, hypotensive lipids, and carbonic anhydrase inhibitors;

antiallergenic agents such as antazoline, methapyriline, chlorpheniramine, pyrilamine and prophenpyridamine;

antiinflammatory agents such as hydrocortisone, leflunomide, dexamethasone phosphate, fluocinolone acetonide, medrysone, methylprednisolone, prednisolone phosphate, prednisolone acetate, fluoromethalone, betamethasone, triamcinolone acetonide, adrenalcortical steroids and their synthetic analogues, and 6-mannose phosphate;

antifungal agents such as fluconazole, amphotericin B, liposomal amphotericin B, voriconazole, imidazole-based antifungals, triazole antifungals, echinocandin-like lipopeptide antibiotics, lipid formulations of antifungals;

polycations and polyanions such as suramine and protamine;

decongestants such as phenylephrine, naphazoline, and tetrahydrazoline;

anti-angiogenesis compounds including those that can be potential anti-choroidal neovascularization agents such as 2-methoxyestradiol and its analogues (e.g., 2-propynl-estradiol, 2-propenyl-estradiol, 2-ethoxy-6-oxime-estradiol, 2-hydroxyestrone, 4-methoxyestradiol), VEGF antagonists such as VEGF antibodies and VEGF antisense, angiostatic steroids (e.g., anecortave acetate and its analogues, 17-ethynylestradiol, norethynodrel, medroxyprogesterone, mestranol, androgens with angiostatic activity such as ethisterone);

adrenocortical steroids and their synthetic analogues including fluocinolone acetonide and triamcinolone acetonide and all angiostatic steroids;

immunological response modifying agents such as cyclosporine A, Prograf (tacrolimus), macrolide immunosuppressants, mycophenolate mofetil, rapamycin, and muramyl dipeptide, and vaccines;

anti-cancer agents such as 5-fluoroucil, platinum coordination complexes such as cisplatin and carboplatin, adriamycin, antimetabolites such as methotrexate, anthracycline antibiotics, antimitotic drugs such as paclitaxel and docetaxel, epipdophylltoxins such as etoposide, nitrosoureas including carmustine, alkylating agents including cyclophosphamide; arsenic trioxide; anastrozole; tamoxifen citrate; triptorelin pamoate; gemtuzumab ozogamicin; irinotecan hydrochloride; leuprolide acetate; bexarotene; exemestrane; epirubicin hydrochloride; ondansetron; temozolomide; topoteanhydrochloride; tamoxifen citrate; irinotecan hydrochlorise; trastuzumab; valrubicin; gemcitabine HCL; goserelin acetate; capecitabine; aldesleukin; rituximab; oprelvekin; interferon alfa-2a; letrozole; toremifene citrate; mitoxantrone hydrochloride; irinotecan HCL; topotecan HCL; etoposide phosphate; gemcitabine HCL; and amifostine;

antisense agents;

antimycotic agents;

miotic and anticholinesterase agents such as pilocarpine, eserine salicylate, carbachol, diisopropyl fluorophosphate, phospholine iodine, and demecarium bromide;

mydriatic agents such as atropine sulfate, cyclopentane, homatropine, scopolamine, tropicamide, eucatropine, and hydroxyamphetamine;

differentiation modulator agents;

sympathomimetic agents such as epinephrine;

anesthetic agents such as lidocaine and benzodiazepam;

vasoconstrictive agents;

vasodilatory agents;

polypeptides and protein agents such as angiostatin, endostatin, matrix metalloproteinase inhibitors, platelet factor 4, interferon-gamma, insulin, growth hormones, insulin related growth factor, heat shock proteins, humanized anti-IL-2 receptor mAb (Daclizumab), etanercept, mono and polyclonal antibodies, cytokines, antibody to cytokines;

neuroprotective agents such as calcium channel antagonists including nimodipine and diltiazem, neuroimmunophilin ligands, neurotropins, memantine and other NMDA antagonists, acetylcholinesterase inhibitors, estradiol and ananlogues, vitamin B12 analogues, alpha-tocopherol, NOS inhibitors, antioxidants (e.g. glutathione, superoxide dismutase), metals like cobalt and copper, neurotrophic receptors (Akt kinase), growth factors, nicotinamide (vitamin B3), alpha-tocopherol (vitamin E), succinic acid, dihydroxylipoic, acid, fusidic acid;

cell transport/mobility impending agents such as colchicine, vincristine, cytochalasin B;

carbonic anhydrase inhibitor agents;

integrin antagonists; and lubricating agents, singly or in combinations thereof.

This listing of therapeutic agents is illustrative, and not exhaustive. Other drugs that could be delivered by the ocular implant include, for example, thalidomide.

Reference can be made to Remington's Pharmaceutical Sciences, Mack Publishing Press, Easton, Pa., U.S.A., to identify other possible therapeutic agents for the eye. Any pharmaceutically acceptable form of the agents can be used, such as the free base form or a pharmaceutically acceptable salt or ester thereof.

Among other things, this invention includes dual mode implants and related treatments effective to saturate all compartments of the eye via large initial loading dose release and then provide a sustained maintenance dosage to the target area of the eye thereafter over an extended period of time. Because the ocular tissues are not homogenous, and also because many drugs to be used in the eye are lipophilic, ideally a large loading dose should be initially delivered by an ocular implant, and once all the tissues of the eye are saturated, then uniform lower yet maintenance levels of the drug need to be released over an extended period of time by the implant which can more easily gravitate to the target areas of the eye for treatment.

The Examples that follow are intended to illustrate, and not to limit, the invention. All percentages used herein are by weight, unless otherwise indicated.

EXAMPLE 1

This example illustrates the preparation of a matrix implant of the invention useful for subconjunctival implants.

4.5 g of superhydrolyzed polyvinyl alcohol (Airvol 125, Air Products and Chemicals, Inc., Allentown, Pa., U.S.A.) was added to 30 ml of molecular biology grade water in an assay tube that was then tightly closed. The tightly closed assay tube was placed in a beaker of boiling water until the density becomes uniform (generally about 3–7 hrs). Since the assay tube was tightly closed, the contents could not evaporate. Water was periodically replaced in the beaker to keep the water height near the height of water in the assay tube. The assay tube was centrifuged for 1 minute at 1000–4000 rpm to degass the mixture. This formed a 15 wt % solution of superhydrolyzed polyvinyl alcohol.

Separate premixtures were prepared using each of cyclosporine A and 2ME2 as the therapeutic agent. Each therapeutic agent was separately premixed in a solution of hydroxypropyl methylcellulose (HPMC), obtained as METHOCEL E4M from Dow Chemical, Midland, Mich., in amount of 0.05 wt % about (on a dry basis; drug plus HPMC). In this regard, 500 mg of drug was combined and mixed with 2.25 g HPMC. For instance, the cyclosporine A (or 2ME2) powder was placed in microbiology grade water (i.e., endotoxin free water) with the HPMC and mixed with a stir bar, no heat, for up to 24 hours. The superhydrolyzed PVA solution was then combined with the HPMC/drug mixture with a spatula. For more highly viscous suspensions, a blender may be desirable. As such a blender, a MiniContainer is adapted to the blender to hold small volumes, where the blender is a Laboratory Blender (Model 51BL30), operated at speeds of 18,000 rpm (low) or 22,000 rpm (high) as needed. The Mini Container (MMGC1) was stainless steel and held 12–37 ml, and was obtained from Waring Factory Service Center, Torrington, Conn. To add the materials to a blender, a bottom of the assay tube containing the PVA/METHOCEL/drug mixture is cut with a razor blade and the contents poured into the blender. In one method, the mixture is blended at high speed (22K RPM) for up to 5 minutes, and the blended contents are then poured into a 50 ml assay tube and centrifuged for 2 minutes at 1000–4000 rpm to degas it.

The resulting highly viscous superhydrolyzed PVA/HPMC/drug mixtures were injected with a large volume syringe between 2 glass plates (6×6 inches). Spacers (1–5 mm thick) were placed between the glass plates. This allowed a measured thickness of mixture to be applied to the glass plate. This complex was the placed at 0° C. for up to 30 minutes. Chilling the glass plates sufficient that the top glass plate could be removed without impairing the matrix layer. The top plate was removed in this manner. The mixture was then left attached to the other bottom glass plate and allowed to air dry at room temperature for approximately 15 hours.

To make dual mode subconjunctival matrix implants, compressed drug pellets were formed to the desired dimensions using a Parr pellet press (Parr Instrument Co., Moline, Ill., USA). Also, before the above-mentioned chilling step performed on the glass plates, the top glass plate was temporarily moved sufficient to permit access to the surface of the wet coating so that the pellet could be lightly pushed or tapped on its upper surface, such as using a Bowman's probe, into the wet coating layer deep enough that the pellet is completely immersed and embedded within the coating layer. At least one mm coating is provided on each side of the pellet in this example, although smaller uniform thicknesses could be used. The top glass plate was replaced again over the surface of the coating layer (now containing the embedded pellet), and the glass plates were chilled as described above. Then, the top glass plate was removed.

After the slab had dried for about 15 hours, trephines (skin Biopsy Punches) (Acuderm Inc., Ft. Lauderdale, Fla.) of varying diameters were used to make the implants. A trephine of dimensions of at least 1 mm greater than pellet diameter was used to punch out pellets. The punched pieces were permitted to sit for 48 additional hours and then irradiated with a low dosage of (e.g., about 3 megarads of gamma radiation) for sterilization purposes only, such that significant levels of crosslinking does not occur.

EXAMPLE 2

This example illustrates the preparation of another matrix implant of the invention, which is useful as an intravitreal implant. Alternatively, this matrix implant can be used for an inlay used in combination with reservoir implants of the invention described elsewhere herein.

Preparation of 50% superhydrolyzed PVA, 6% 2ME2, 0.05% HPMC matrix implant:

The polymer drug mixture was prepared in a 3 cc syringe (the tip sealed with a Luer lok and a HPLC septum). The plunger was removed. A drug emulsion was prepared by adding 63.8 mg 2ME2 and 0.5 mg hydroxypropyl methylcellulose (E4M, Dow Chemical) to 2 ml molecular grade biological water. The emulsion was mixed with a magnetic stirrer over night, and then it was added to 1 g superhydrolyzed PVA (Airvol 125; Air Products and Chemicals, Inc., Allentown, Pa., U.S.A.) in the syringe. The mixture was stirred until uniform and then placed into a water bath at about 100° C. for 60 minutes. The sample with the syringe was then spun down for 2 minutes at 2000 rpm to dislodge air bubbles. It was then returned to the 100° C. water bath for 15 minutes to make it pliable. The original plunger was inserted into the syringe and a small hole was made just above the drug/polymer sample to prevent reintroduction of air into the sample. The tip of the syringe was then cut off and the sample ejected onto a glass plate. Using spacers, another plate is used to sandwich the sample the resulting sandwich is then cooled at 5° C. for 30 minutes. The glass plates were separated and the sample dried under ambient conditions for 24 hours and then under vacuum for 48 hours. The implants were then cut to size using a razor blade. For dual mode implants made from this slab, 0.5 mm drug pellets (generally 0.3 to 1.0 mm long and about 100 μg to 500 μg) were inserted into the space between the glass plates before refrigerating. This was done by placing the pellets in the coating layer at the edges thereof where the two glass plates come together and the coating layer is exposed. Once the PVA slab was desiccated, the dual action implants were cut in the desired shape (e.g., circular) leaving the desired amount of drug loaded PVA around the drug pellet.

EXAMPLE 3

A 1×1×2 mm matrix implant was prepared using poly (ethylene vinyl) acetate (EVA) in place of superhydrolyzed PVA in the subconjunctival implant.

Preparation of 30% EVA, 6% $2ME_2$, 0.05% HPMC matrix implants:

The polymer drug mixture was prepared in a 3 cc syringe (the tip sealed with a Luer lok and a HPLC septum). The plunger is removed. A drug emulsion is prepared by adding 38.3 mg 2ME2 and 0.3 mg HPMC (E4M, Dow Chemical)

to 2 ml methylene chloride. The emulsion is mixed over night with a magnetic stirrer and then transferred to a 10 ml vial containing 0.6 g EVA (Elvax 40W, Dupont). The mixture was stirred with a magnetic stirrer until it becomes too viscous. The magnetic stirrer was then removed and the mixture was left overnight. The sample was centrifuged as needed to degass the specimen. The specimen was poured onto a glass plate and permitted to dry for 48 hours under vacuum. The implants were then cut to size using a razor blade, e.g., multiple 1×1×2 mm slabs or wafers. For dual mode implants, 0.5 mm drug pellets that are generally 0.3 to 1.0 mm long and about 200 µg) are inserted until fully embedded in a centered manner in the wet EVA/drug mixture after it was poured out on the glass. Once the slab was desiccated, the dual action implants were cut leaving a desired amount of drug loaded EVA around the drug pellet.

EXAMPLE 4

Matrix implants of this invention were used in a study to document the in vitro release rates of single and dual mode CsA implants to evaluate their usefulness for the treatment of eye diseases, such as high risk corneal transplantation. In addition, to evaluate the feasibility of using these implants in humans, rabbit studies were performed to assay the ocular drug levels following the insertion of these implants in the subconjunctival space. The ocular toxicity of these implants were evaluated by electroretinography (a test of retinal function) and histopathology.

Methods:

In Vitro Studies

Two matrix implant designs were studied, i.e. single and dual mode CsA implants, designated Matrix Implant (1) and (2), respectively.

A Matrix Implant (1) was made generally according to the protocol described in Example 1 except without adding the drug pellet. That is, a superhydrolyzed PVA solution made using 4.5 grams of Airvol 125 (Air Products and Chemicals, Inc., Allentown, Pa., U.S.A.), in solution, was combined with 5 ml of an emulsion of CsA. The CsA emulsion was separately previously prepared as a premixture of 0.5 g powdered CsA,(USP-23, Xenos Bioresources, Inc., Santa Barbara, Calif.) and 0.0023 g HPMC (METHOCEL E4M, obtained from Dow Chemical, Midland, Mich.) in 5 ml of microbiology grade water. The combined PVA and CsA/HPMC solutions gave a 10% CsA concentration by weight. The PVA/HPMC/CsA aqueous mixture was mixed at 70° C. for 30 minutes. The PVA/HPMC/drug suspension was placed between glass plates. Upon drying, a uniform film of 0.5-mm thickness was produced in the manner described in Example 1. A 3-mm trephine was used to cut circular implant discs from the resulting film.

Matrix Implant (2) was made using the same procedure as above except a 1.5 mg compressed CsA drug pellet of a thickness of 2.0 mm was embedded within the center of the circular disc. To embed the pellet, the pellet was embedded within the coating layer in the manner described in Example 1.

In-vitro release rates were determined by placing the implants in PBS (pH 7.4) at 37° C. and assaying drug levels over time by HPLC.

In Vivo Studies:

Ocular Drug Levels:

Eight New Zealand White rabbits (16 eyes) of either sex weighing 2–3 kg were used in this study and the procedures adhered to the guidelines from the Association for Research in Vision and Ophthalmology for animal use in research. Animals were anesthetized with ketamine hydrochloride (Fort Dodge, Inc., Fort Dodge, Ind.) (35 mg/kg) IM, xylazine (Phoenix Scientific, Inc., St. Joseph, Mo.) (5 mg/kg) IM, and proparacaine 1% ophthalmic drops (Allergan America, Hormigueros, Puerto Rico) were used topically on the eye. A lid speculum was placed and a 4 mm conjunctival radial incision was made through the conjunctiva 1 mm from the limbus and 3 mm nasal to the superior rectus muscle. Wescott scissors were used to dissect posterior to Tenon's fascia and the implant was inserted with its anterior edge 3 mm from the limbus and secured to the episclera using a single interrupted 10-0 suture. The conjunctiva was reapproximated using a running 10-0 suture. In vivo studies were performed using the dual mode CsA implant because of its potential to release CsA for an extended period of time to treat eye diseases. The right eye of each rabbit received a dual mode CsA implant. Postoperatively, bacitracin-neomycin-polymyxin ophthalmic ointment (Pharmaderm, Melville, N.Y.) was placed in both eyes twice daily (2×/day) for 3 days. The animals were examined regularly and euthanized with a pentobarbital overdose (Beuthanasia-D Special, Scheming-Plough Animal Health Corp., Kemilworth, N.J.) 2 months post-implantation. Both eyes were enucleated. Eyes from 5 rabbits had a 5×5 mm section of conjunctiva both over the implant and 180° away isolated for drug extraction. The implants were firmly attached to the episclera and they were gently peeled away from the underlying tissues. The globes were immediately frozen at −70° C. for later dissection and drug extraction. The time from enucleation to freezing was rapid (<10 seconds) which limited postmortem drug redistribution. The eyes were dissected while frozen and a 5'5 mm section of full thickness sclera beneath the implant and 180° away was isolated. Other tissues (cornea, aqueous humor, lens, and vitreous humor) were isolated for separate drug analysis. The CsA was extracted from the tissues by the addition of an equivalent weight of HPLC grade Acetonitrile (Burdick & Jackson, Inc., Muskegon, Mich.), sonicated for 45–90 seconds with a model GEX 600 Ultrasonic processor (Thomas Scientific, Swedesboro, N.J.) and incubated for 24 hours at room temperature. The samples were spun down in a TOMY MTX-150 centrifuge (Peninsula Laboratories Inc., Belmont, Calif.) for 30 minutes at 10,000 rpm and the supernatants were submitted for HPLC analysis. The CsA concentrations in the tissues were expressed as µg/g wet weight (mean) for the solid tissues and µg/ml (mean) for the aqueous and vitreous humor.

Eyes from 3 rabbits were placed in formalin 10% (Biochemical Science, Inc., Swedesboro, N.J.) for at least 7 days, embedded in paraffin, and sectioned for histopathology.

Ocular Toxicity Testing (Electroretinography):

The rabbits were anesthetized using the same procedures detailed above and the pupils were dilated with 1 drop of phenylephrine hydrochloride 2.5% (Akorn, Inc., Decatur, Ill.) and tropicamide 1% (Alcon, Inc., Humacao, Puerto Rico). ERGs were recorded from each eye separately after 30 minutes of dark adaptation. A monopolar contact lens electrode (ERG-jet, La Chaux des Fonds, Switzerland) was placed on the cornea and served as a positive electrode. Subdermal needle electrodes inserted in the forehead area and near the outer canthus served as the ground and negative electrodes, respectively. ERGs were elicited by flash stimuli delivered with a Grass PS22 photostimulator (Grass Instruments, Quincy, Mass.) at 0.33 Hz. Responses were amplified, filtered and averaged with a Nicolet Spirit signal averager (Nicolet Instruments Corp., Madison, Wis.). Averages of 20 responses were measured to obtain amplitude and implicit time values of a-waves and b-waves. Recordings were performed at baseline, and 1 and 2 months post-implantation. A permutation test of mean amplitude differences and analysis of variance of the logarithmic transform of amplitudes were performed to determine statistically significant changes between readings.

Results:

The single mode Matrix Implant (1) produced an initial loading dose of CsA (12.54+/−1.47 µg/day) with a logarithmic decline to <0.5 µg/day by day 31 (see FIG. 4A), while Matrix Implant (2) produced an initial loading dose of CsA (39.9+/−10 µg/day) with a logarithmic decline in release rate to 7.67+/±1.79 µg/day by day 38 (FIG. 4B). Daily release rates reached a steady state release of 6 µg/day after day 40 and the release rates were predicted to be stable for 18 months.

CsA Levels in Tissues:

Five rabbits had the eye with the dual mode CsA implant processed to determine CsA concentrations. The distribution of the CsA in the eye is shown in FIG. 13. Corneal levels of 2.25 µg/g (mean) were present which are potentially therapeutic for the treatment of graft rejection. Unexpectedly, an unusually high concentration of CsA was present in the vitreous (21.78 µg/ml (mean)) which can potentially be therapeutic for the treatment of posterior segment inflammatory diseases.

Ocular Toxicity Testing:

Electroretinography showed no signs of retinal toxicity from the CsA implants. Histopathologic examination of eyes from 3 rabbits with the dual mode implant was performed by light microscopy. The conjunctiva overlying the implant and the sclera beneath was intact. All ocular structures appeared intact with a mild chronic inflammatory infiltrate present in the substantia propia of the conjunctiva overlying the implants in all eyes. The peripheral retina anterior to the equator showed some vacuolated spaces predominantly in the photoreceptor layer in both eyes but the photoreceptor layer in the posterior segment of the eye along the medullary rays was normal.

Conclusions:

These results demonstrated that single mode Matrix Implant (1) subconjunctival implant can deliver potentially therapeutic levels of CsA to the eye for approximately a month. The dual mode Matrix Implant (2) subconjunctival implant could deliver an initial loading dose of CsA lasting 1 month followed by a steady state sustained-release delivery of CsA as a maintenance dose for at least 1 year. The implants were determined to be reasonably safe by histopathological examination and by electroretinography.

The implant was initially designed to release CsA into the cornea for prevention of graft rejection in patients with high risk corneal allografts. To this end, the implants delivered potentially therapeutic levels of CsA to the cornea. This study revealed an unexpected finding that the dual mode implant representing an embodiment of this invention delivered high levels of CsA in the vitreous cavity. Since the vitreous cavity is in direct contact with the retina and the other important tissues of the eye, the subconjunctival implant (which is installed outside the eye) has the potential to treat many intraocular diseases.

EXAMPLE 5

A study was performed to investigate the use of 2-methoxyestradiol in intravitreal matrix implants of this invention in a rat model of choroidal neovascularization (CNV).

Methods:

Implant Design:

2ME2 dry powder was premixed in a solution containing 0.05% HPMC then mixed with a 50% polyvinyl alcohol (PVA) solution to produce a 6% (by dry weight) 2ME2 matrix suspension (see example 2 for details). The suspension was poured onto a glass plate producing a thin film, dried at room temperature, and cut into 1.0×1.0×2.0 mm sections, each section representing one implant. Sham implants (PVA without drug) were made in a similar fashion. In-vitro release rates were determined by placing the implants in PBS and assaying drug concentrations over time with HPLC.

CNV Model:

Fifteen Brown-Norway rats were used. An E1-deleted adenoviral vector encoding human VEGF165 was injected ($2.5 \times 10^4$ pfu/µL) into the subretinal space nasal to the disc of one eye using a 32 gauge needle. In the same eye, a 2 mm full-thickness scleral incision was made temporally and 2ME2 implants were placed in the vitreous cavity of 9 eyes and sham implants placed in 8 eyes. The sclerotomy was closed using a 10-0 nylon suture. Five rats (3 with 2ME2 and 2 with sham implants) were euthanized at 1 week. Five rats (2 with 2ME2 and 3 with sham implants) were euthanized at 2 weeks. Five rats (2 with 2ME2 and 3 with sham implants) were euthanized at 3 weeks. The implant eyes were enucleated, fixed in formalin and embedded in methacrylate-JB4. The eyes were sectioned in the area of injection (75 total, 3 µm sections), counterstained with H&E and examined with a light microscope for choroidal neovascularization. The maximal axial length of the CNV was recorded in micrometers.

Figure 15:
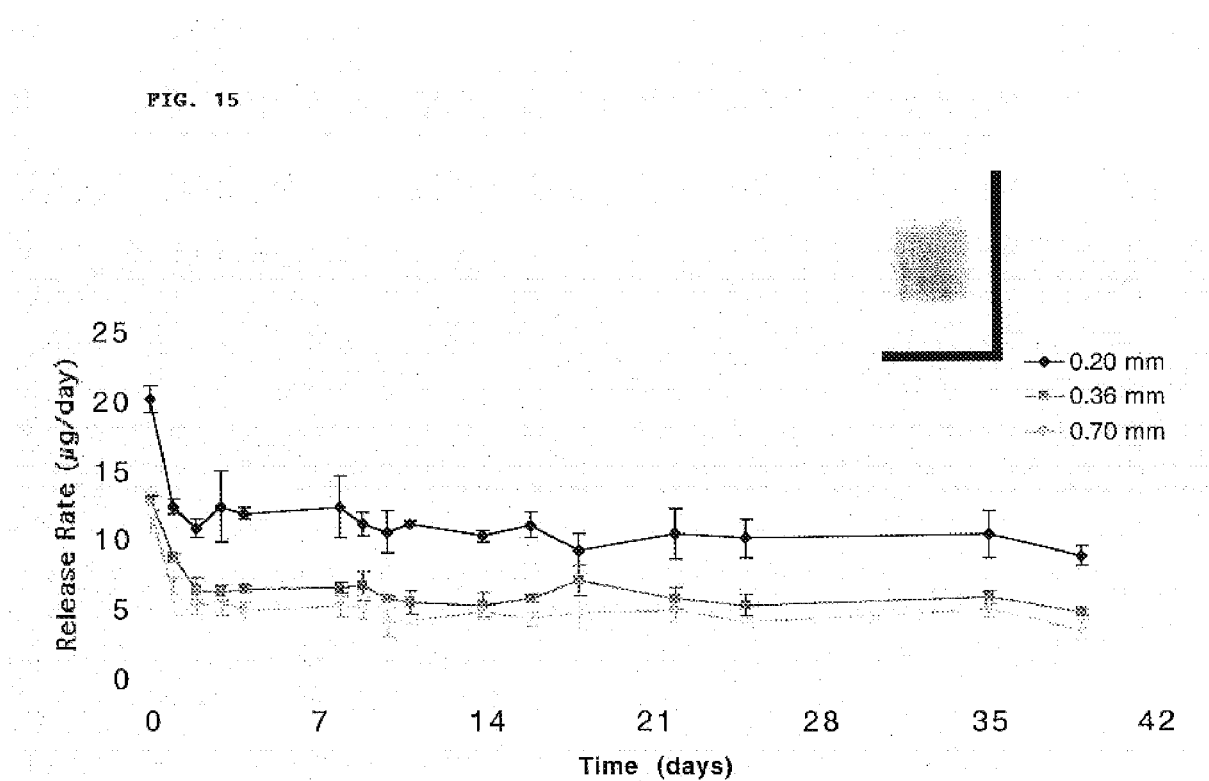
FIG. 15 graphically illustrates the in vitro release rates of a drug (2ME2) according to reservoir implants of this invention that varies the polymer thickness surrounding the drug pellet, as described in Example 6 herein.

Results:

In vitro Release Rates of 3 Implants:

The mean in-vitro release rates (graph below) followed first-order kinetics, typical of matrix implants. The implants released 2ME2>1 µg/day over 30 days, as shown in FIG. 15.

CNV Model:

CNV was present in 1/9 eyes with the 2ME2 implant: the axial length of the one membrane=46.5 µm. A proliferation of RPE cells in a bi or tri-layer was present in all 3 eyes at 1 week. CNV was present in 5/8 eyes with the sham implant: mean axial length=347.4 µm.

Results:

These results demonstrated that the sustained-release 2ME2 microimplants representing this invention can successfully suppress choroidal neovascularization in a rat model.

EXAMPLE 6

The dual mode reservoir implants were made and tested in vitro for release rate behavior.

Methods:

Three designs were constructed using 2ME2 compressed in a customized Parr pellet press to 190 lb force.

Design Summary:

Design A: A 2ME2 pellet (3 mm, mean weight 23.0 mg) was coated with 0.20 mm silicone (using 8 gauge, 3.28 mm internal diameter PTFE (Teflon) tubing from Texloc, LTD. Fort Worth, Tex.);

Design B: A 2ME2 pellet (2 mm, mean weight 10.5 mg) was coated with 0.36 mm silicone (using 10 gauge, 2.59 mm internal diameter PTFE tubing);

Design C: A 2ME2 pellet (2 mm, mean weight 10.5 mg) was coated with 0.70 mm silicone (using 8 gauge, 3.28 mm internal diameter PTFE tubing)

A microcentrifuge having an ID of about 10 mm and a length of about 40 mm, was obtained from Peninsula Laboratories Inc., Belmont, Calif. U.S.A. The microcentrifuge tube was filled with MED-6810 about 10 mm in depth.

To make uniform silicone coatings of 0.20 mm, 0.36 mm and 0.70 mm around the drug pellets, thin walled plastic tube (PTFE teflon tubing from Texloc, LTD. Fort Worth, Tex.) was used. The PTFE tubing was heated at 110 degrees celsius for 30 seconds and then straightened, cut into 1.0 inch (2.54 cm) long tubes, and thereafter cooled and set in the straightened orientation in the microcentrifuge tube. The microcentrifuge tube was centrifuged to degas the wet silicone and to radially center the PTFE tube. The silicone was then cured with heat (100° C. for 30 minutes). The pellet sizes and PTFE tubing diameters used for the 3 designs are detailed supra.

The 2ME2 drug pellet was introduced into the PTFE tubing followed by adding additional fresh MED-6810 silicone sufficient to immerse the pellet. The microcentrifuge tube was then centrifuged as needed to degas the additional silicone. As needed, the drug pellet was manually or mechanically centered on the silicone base before curing the added silicone using a Bowman probe. Drug loading was performed using the 'delay in cure' technique. That is, the pellets were left in the wet silicone for a total of 1 hour and then cured for 1 hour at 100° C.

In vitro release rates were determined by placing the implants in 20 mL of phosphate buffered saline pH 7.4 maintained at 37° C. for 3 hours. The concentration of 2ME2 in the vial was determined by HPLC and the release rates of drug from the implants were recorded as µg/day (microgram/day).

Results:

The release rates for the different implant designs are shown in FIG. 15. FIG. 16 tabulates the results. As was demonstrated, dual mode reservoir implants representing this invention can be manufactured to release predictable loading and maintenance doses. Using the delay in cure technique effectively loads the surrounding silicone for the burst effect and changing the thickness of the silicone coating surrounding a 2ME2 drug pellet can alters the maintenance release rate of the implant. Design B was chosen for the rabbit studies, described in Example 7 infra, because of its superior durability, optimal release rate, and desirable life span.

EXAMPLE 7

To evaluate the feasibility of using the implants of this invention for human diseases, such as choroidal neovascularization, rabbit studies were performed using 2ME2 intravitreal implants. Drug extraction techniques were done to assay the ocular drug levels following the insertion of these implants in the vitreous cavity. The ocular toxicity of these implants were evaluated by electroretinography (a test of retinal function) and histopathology.

2ME2 powder was obtained from EntreMed Inc., Rockville, Md. For this study, we chose a dual mode reservoir implant of Design B releasing 2ME2 as described in Example 6.

Ocular Drug Levels:

Seven rabbits had 2ME2 implants (Design B) surgically placed in the vitreous cavity of the right eye as follows: All procedures on animals were performed in accordance with protocols approved by the Animal Care and Use Committee. Male and female New Zealand white rabbits, weighing 2–3 kg were anesthetized with intramuscular ketamine (35 mg/kg) and xylazine (5 mg/kg). One drop of proparicaine (1%) was placed in the inferior fornix for topical anesthesia, and the pupils were dilated with 1 drop of phenylephrine hydrochloride (2.5%) and topicamide (1%). Using sterile procedures, a lid speculum was placed in the right eye, and a fornix-based conjunctival flap was made in the superotemporal quadrant. A 4 mm sclerostomy was made 3 mm posterior to the surgical limbus. The drug implant was inserted through the incision into the vitreal cavity. Prolapsed vitreous was excised as needed using a weck cell vitrectomy technique. The sclerostomy was closed using 8-0 nylon and the conjunctiva was reapproximated to the limbus using 10-0 vicryl. The eye was injected with balanced salt solution as necessary to normalize the intraocular pressure. Indirect ophthalmoscopy was done to confirm placement of the implant in the vitreal cavity. Bacitracin ophthalmic ointment was applied twice daily for three days.

Four rabbits were sacrificed at 1 month post-implantation and 3 rabbits at 3 months. The right eye of each rabbit was removed and the tissues processed for 2ME2 drug levels. Following enucleation the eyes were frozen at −80° C. in order to prevent drug redistribution. The drug extraction procedure was as follows: the eyes were dissected while frozen and an equal weight of acetonitrile was added to extract the drug from the aqueous humor, vitreous humor, and blood. The specimens were sonicated, centrifuged, and the drug levels in the supernatant determined by HPLC.

Ocular Toxicity Testing:

The details of the electroretinography procedure in rabbit is described in Example 4. Six NZW rabbits had 2ME2 implants (Design B) surgically placed in the vitreous cavity of the right eye (OD) and a sham implant in the left eye (OS). The rabbits had their eyes examined clinically and serial electroretinography (ERG) performed to assess for drug toxicity over a 6 month period. The rabbits were sacrificed at 6 months post-implantation and their eyes were processed for histopathology. The results are summarized below.

Figure 17:
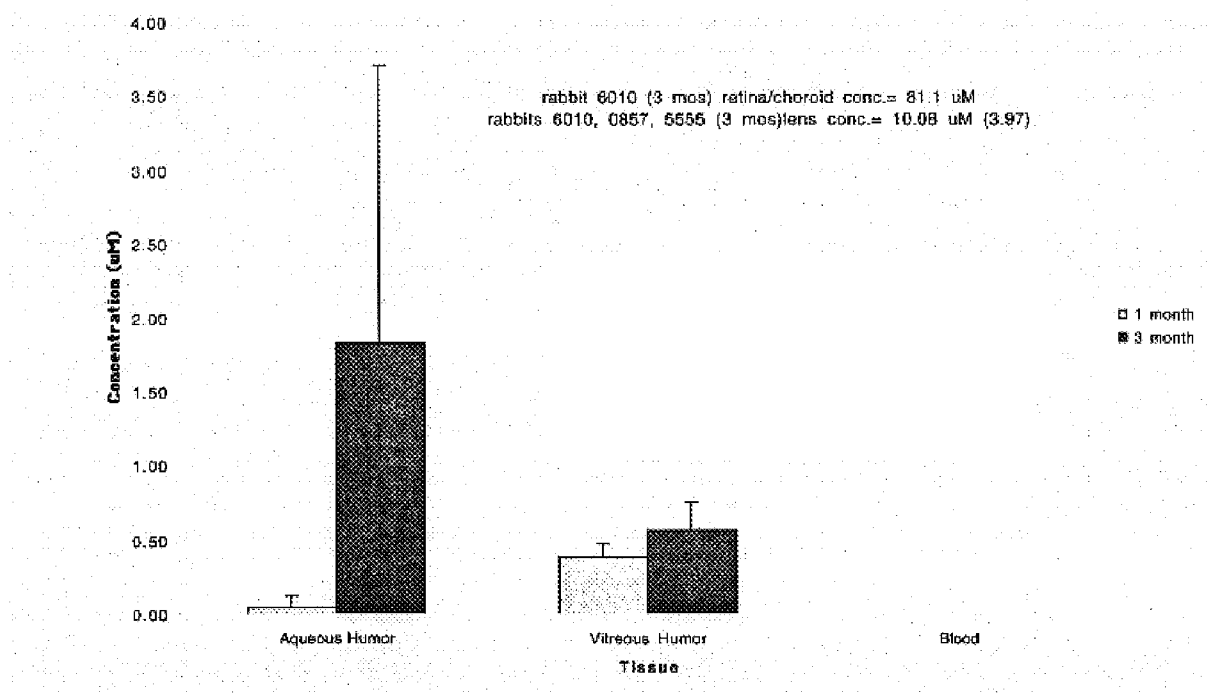
FIG. 17 graphically illustrates the levels of 2ME2 in the aqueous humor, vitreous humor and blood in rabbits at one and three months after receiving an intravitreal reservoir dual mode implant according to the invention, as described in Example 7.

Ocular and Blood Drug Levels:

The 2ME2 levels in the vitreous humor, the tissue that has intimate contact with the retina, were in the therapeutic range for the control of angiogenesis (see FIG. 17). There was no detectable level of 2ME2 in the blood.

Ocular Toxicity:

The electroretinograms showed no abnormalities over the 6 month period. The clinical examinations and histopathology showed no signs of ocular toxicity.

Results:

The 2ME2 levels in the vitreous treated with implants representing this embodiment of the invention are potentially therapeutic levels to treat choroidal neovascularization. Since there were no detectable drug levels in the blood of these rabbits, the risk of systemic toxicity from drug released by the ocular implant are negligible.

EXAMPLE 8

A study was performed to compare the efficacy in a rat model of choroidal neovascularization (CNV) of triamcinolone acetonide (TAAC) in intravitreal matrix implants of this invention to a comparison implant.

Methods:

Implant design:

Design A1: (comparison reservoir design):

A compressed TAAC pellet (0.5 mm diameter at 120 lb-force) was coated with medical grade silicone (final implant dimensions 1×2.5 mm).

Design B1: (single mode matrix design according to this invention):

TAAC dry powder was premixed with 0.05% HPMC then mixed with a 20% polyvinyl alcohol (PVA) solution to produce a 5% (by dry weight) TAAC matrix suspension (see example 2 for details). The suspension was poured onto a glass plate producing a thin film, dried at room temperature, and cut into 1×1×2.5 mm sections, each section representing one matrix implant.

In-vitro release rates were determined by placing the implants in PBS and assaying drug concentrations over time with HPLC.

CNV Model:

To induce experimental CNVM formation, a series of 8 laser photocoagulation sites were concentrically placed around the optic disk (of 1 eye) followed by surgical placement of either a Design A1, Design B1, or sham implant (3 animals minimum in each group). The surgical procedure for implant insertion was similar to that in Example 5. At 35 days, the eyes were enucleated, fixed in formalin and embedded in methacrylate-JB4. The eyes were sectioned in the area of injection, counterstained with H&E and examined with a light microscope for choroidal neovascularization. The CNVM at each laser burn was quantified by measuring the thickness and the mean value for each eye was recorded.

Results:

In vitro release rates:

Design A1 followed constant release kinetics and the release was 1.96±1.73 µg/day over a 28 day period.

Figure 18:
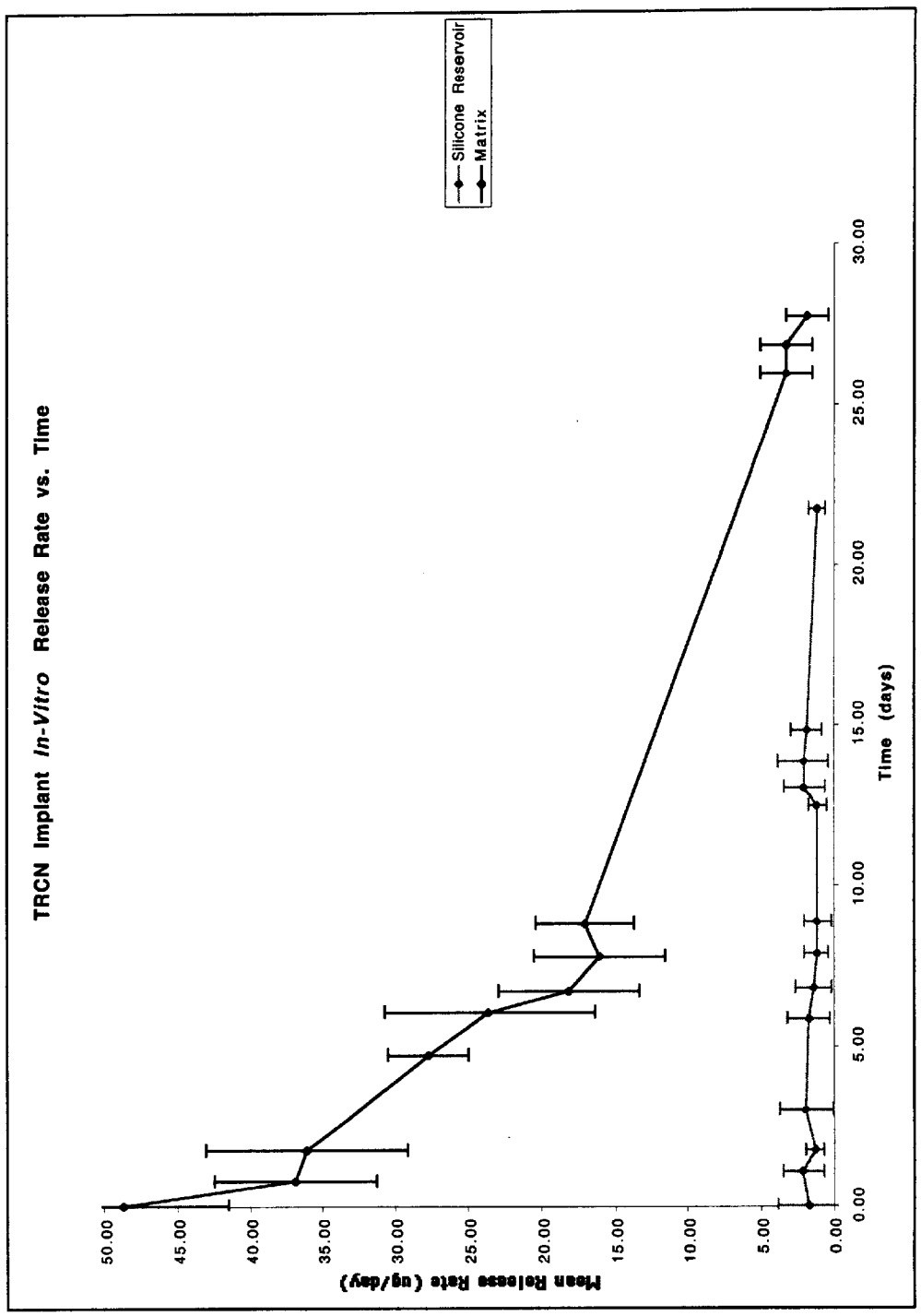
FIG. 18 graphically illustrates the release rates of triamcinolone acetonide (TAAC) according to an embodiment of the invention and a comparison implant in a rat model of induced CNVM, as described in Example 8.

Design B1 followed first-order kinetics with an initial release rate of 42.88±1.24 µg/day over the initial 48 hours; decreasing to 1.94±1.46 µg/day by day 28. These results are graphically shown in FIG. 18.

CNV Model:

In the eyes with the sham implants, CNV development was very rapid and occurred at 3–7 days after lesion induction and was sustained over 4 weeks. The mean CNVM thickness at 35 days with the sham implant (no drug) was 55±10 µm. The mean values for eyes with Design A implant was 35–50 µm; Design B implant, 15–20 µm.

Results:

These results demonstrate that Design B1, a single mode matrix design representing an embodiment of this invention, was more effective in suppressing CNV in a rat laser model compared with a comparative reservoir device representing the prior art. Design B1 implants delivered a large loading dose of drug that may be more effective for the treatment of CNV than the low dose delivery of implant representing the prior art. Most effective for human may be a loading dose of an angiostatic steroid followed by a low dose maintenance delivery to promote dormancy of the lesion over time. However, rat models of CNV only last 4–5 weeks and these dual mode implants cannot currently be assessed adequately.

While the invention has been described in terms of preferred embodiments, those skilled in the art will recognize that the invention can be practiced with modification within the spirit and scope of the appended claims.

What is claimed is:

1. An ocular implant providing sustained-release of a first therapeutic agent to the eye for a prolonged period of time, comprising:
   a composite material matrix layer including:
   (i) a first therapeutic agent,
   (ii) a polymeric matrix material into which the first therapeutic agent is dispersed, including (1) a bio-erodible polymer permeable to the therapeutic agent, the permeable polymer being superhydrolyzed polyvinyl alcohol, and (2) a water-soluble polymer having greater water solubility than the permeable polymer, the water-soluble polymer being a cellulose ether polymer, and
   (iii) a discrete solid core containing the first or a second therapeutic agent, the therapeutic agent being dispersed, and the solid core being embedded within the composite material matrix layer.

2. The implant according to claim 1, wherein the composite material matrix layer comprises about 5 to about 50 wt % of the permeable polymer, about 0.05 to about 90 wt % of the water-soluble polymer, and about 1.0 to about 50 wt % of the first therapeutic agent.

3. The implant according to claim 1, wherein the composite material matrix layer comprises about 5 to about 50 wt % of the superhydrolyzed polyvinyl alcohol, about 0.05 to about 90 wt % of the cellulose ether polymer, and about 1.0 to about 50 wt % of the first therapeutic agent.

4. The implant according to claim 1, wherein the cellulose ether polymer comprises hydroxyalkyl cellulose.

5. The implant according to claim 1, wherein the cellulose ether polymer comprises hydroxypropyl methyl cellulose.

6. The implant according to claim 1, wherein a part of the exterior surface area of the composite material matrix layer is covered by polymethyl methacrylate sufficient to adjust the rate of delivery of the therapeutic agent from the implant to the eye.

7. The implant according to claim 1, wherein the composite material matrix layer comprises about 5 to about 50 wt % superhydrolyzed polyvinyl alcohol.

8. The implant according to claim 1, wherein the therapeutic agent is selected from the group consisting of antibiotic agents, antibacterial agents, antiviral agents, antiglaucoma agents, antiallergenic agents, anti-inflammatory agents, anti-angiogenesis compounds, antiproliferative agents, immune system modifying agents, anti-cancer agents, antisense agents, antimycotic agents, myotic agents, anticholinesterase agents, mydriatic agents, differentiation modulator agents, sympathomimetic agents, anaesthetic agents, vasoconstrictive agents, vasodillatory agents, decongestants, cell transport/mobility impending agents, polypeptides and protein agents, steroidal agents, carbonic anhydrase inhibitor agents, polycations, polyanions, lubricating agents, and mixtures thereof.

9. An ocular implant providing sustained-release of a therapeutic agent to the eye for a prolonged period of time, comprising:
   (a) a composite material matrix layer including:
   (i) a first therapeutic agent, and
   (ii) a polymeric matrix material into which the first therapeutic agent is dispersed, including poly (ethylene vinyl) acetate and a cellulose ether polymer, and
   (b) optionally, a discrete solid core containing an additional amount of the first therapeutic agent or a second different therapeutic agent, wherein said solid core being embedded within the composite material matrix layer.

10. A method of delivering a therapeutic agent to an eye in need of treatment thereof, comprising attaching an implant containing a therapeutic agent to the eye, wherein the implant comprises a composite material matrix layer including a therapeutic agent, and a polymeric matrix material into which the therapeutic agent is dispersed including a superhydrolyzed polyvinyl alcohol permeable to the therapeutic agent and a cellulose ether polymer, and, optionally, a discrete solid core containing additional therapeutic agent and embedded within the composite material matrix layer, effective to deliver the therapeutic agent to the eye.

11. The method of claim 10, wherein the implant is attached to a subconjunctival region of the eye.

12. The method of claim 10, wherein the implant is attached to an intravitreal region of the eye.

13. The method of claim 10, wherein the discrete solid core is included, and delivery of the therapeutic agent proceeds as an initial loading dose delivery followed by sustained release of a lower, relatively constant rate of infusion.

14. The method of claim 10, wherein the therapeutic agent in the composite material matrix layer and the discrete solid core comprises cyclosporine.

15. The method of claim 12, wherein the implant is attached to a subconjunctival region of the eye, and wherein therapeutic agent is delivered in an amount effective for corneal allograft therapy.

16. The method of claim 10, wherein the therapeutic agent in the composite material matrix layer and the pellet comprises 2-methoxyestradiol.

17. The method of claim 12, wherein the implant is attached to an intravitreal region of the eye, and wherein therapeutic agent is delivered in an amount effective for treatment of chordial neovascular membranes CNVM.

18. The method of claim 10, wherein treatment is performed on the eye of a mammalian organism.

* * * * *